United States Patent
Millett et al.

(10) Patent No.: US 10,076,301 B2
(45) Date of Patent: Sep. 18, 2018

(54) DEVICES, SYSTEMS, AND METHODS FOR ASSESSMENT OF VESSELS

(71) Applicant: Volcano Corporation, San Diego, CA (US)

(72) Inventors: Bret C. Millett, Folsom, CA (US); Joe Burnett, Carlsbad, CA (US); Howard David Alpert, El Dorado Hills, CA (US); Fergus Merritt, El dorado Hills, CA (US)

(73) Assignee: VOLCANO CORPORATION, San Diego, CA (US)

( * ) Notice: Subject to any disclaimer, the term of this patent is extended or adjusted under 35 U.S.C. 154(b) by 5 days.

(21) Appl. No.: 14/144,280

(22) Filed: Dec. 30, 2013

(65) Prior Publication Data
US 2014/0187920 A1 Jul. 3, 2014

Related U.S. Application Data

(60) Provisional application No. 61/747,480, filed on Dec. 31, 2012.

(51) Int. Cl.
*A61B 6/00* (2006.01)
*A61B 5/00* (2006.01)
(Continued)

(52) U.S. Cl.
CPC .......... *A61B 6/5247* (2013.01); *A61B 5/0066* (2013.01); *A61B 5/0084* (2013.01);
(Continued)

(58) Field of Classification Search
CPC ......... A61B 6/504; A61B 8/12; A61B 5/0066; A61B 8/0891; A61B 6/5247
See application file for complete search history.

(56) References Cited

U.S. PATENT DOCUMENTS

| 7,930,014 B2 | 4/2011 | Huennekens et al. |
| 8,290,228 B2 | 10/2012 | Cohen et al. |

(Continued)

FOREIGN PATENT DOCUMENTS

| JP | 2006-518623 A | 7/2007 |
| WO | WO 2008/107905 | 9/2008 |
| WO | WO 2012/164481 | 12/2012 |

OTHER PUBLICATIONS

International Search Report and Written Opinion received in Patent Cooperation Treaty Application No. PCT/US2013/078321, dated Apr. 24, 2014, 13 pages.

(Continued)

*Primary Examiner* — Tse Chen
*Assistant Examiner* — Jason Ip

(57) ABSTRACT

Devices, systems, and methods for visually depicting a vessel and evaluating treatment options are disclosed. A method of evaluating a vessel of a patient, comprises: obtaining intravascular data from an intravascular instrument positioned within a vessel of a patient while the intravascular instrument is moved longitudinally through the vessel from a first position to a second position; obtaining an angiographic image of the vessel while the intravascular instrument is moved longitudinally through the vessel; correlating the intravascular data from the intravascular instrument to locations on the angiographic image; and outputting an enhanced angiographic image of the vessel on a display, the enhanced angiographic image including the angiographic image overlaid with visualizations representing the intravascular data at the correlated locations. Corresponding systems are also provided.

20 Claims, 15 Drawing Sheets

(51) Int. Cl.
  *A61B 5/0215* (2006.01)
  *A61B 8/12* (2006.01)
  *A61B 8/08* (2006.01)
  *A61B 8/00* (2006.01)
  *A61B 5/02* (2006.01)
  *A61B 5/027* (2006.01)
  *A61B 5/026* (2006.01)

(52) U.S. Cl.
  CPC ........ *A61B 5/02007* (2013.01); *A61B 5/0215* (2013.01); *A61B 5/7425* (2013.01); *A61B 6/4417* (2013.01); *A61B 6/504* (2013.01); *A61B 8/0891* (2013.01); *A61B 8/12* (2013.01); *A61B 8/4416* (2013.01); *A61B 8/5261* (2013.01); *A61B 5/026* (2013.01); *A61B 5/027* (2013.01); *A61B 5/743* (2013.01); *A61B 6/463* (2013.01)

(56) References Cited

U.S. PATENT DOCUMENTS

| | | |
|---|---|---|
| 8,781,193 B2 | 7/2014 | Steinberg et al. |
| 9,339,348 B2 | 5/2016 | Davies et al. |
| 2002/0115931 A1 | 8/2002 | Strauss et al. |
| 2006/0052700 A1* | 3/2006 | Svanerudh ........... A61B 5/0215 600/438 |
| 2006/0165270 A1 | 7/2006 | Borgert et al. |
| 2006/0241465 A1 | 10/2006 | Huennekens et al. |
| 2007/0038061 A1 | 2/2007 | Huennekens et al. |
| 2007/0038081 A1 | 2/2007 | Eck et al. |
| 2007/0232909 A1* | 10/2007 | Hughes et al. ............... 600/437 |
| 2008/0004530 A1* | 1/2008 | Feldman et al. .............. 600/467 |
| 2008/0221439 A1 | 9/2008 | Iddan et al. |
| 2008/0221440 A1 | 9/2008 | Iddan et al. |
| 2008/0221442 A1 | 9/2008 | Tolkowsky et al. |
| 2011/0075912 A1 | 3/2011 | Rieber et al. |
| 2011/0178413 A1* | 7/2011 | Schmitt et al. ............... 600/478 |
| 2012/0136244 A1* | 5/2012 | Manstrom ........... A61B 5/0215 600/431 |

OTHER PUBLICATIONS

International Searching Authority/European Patent Office, "Communication—Supplementary European Search Report," for European Application No. 13869454.2, dated Jul. 21, 2016, 8 pages.

* cited by examiner ized. Additional aspects, features, and advantages of the present disclosure will become apparent from the following detailed description.
DEVICES, SYSTEMS, AND METHODS FOR ASSESSMENT OF VESSELS

CROSS-REFERENCE TO RELATED APPLICATIONS

The present applications claims priority to and the benefit of U.S. Provisional Patent Application No. 61/747,480, filed Dec. 31, 2012, which is hereby incorporated by reference in its entirety.

TECHNICAL FIELD

The present disclosure relates generally to the assessment of vessels and, in particular, the assessment of the severity of a blockage or other restriction to the flow of fluid through a vessel. Aspects of the present disclosure are particularly suited for evaluation of biological vessels in some instances. For example, some particular embodiments of the present disclosure are specifically configured for the evaluation of a stenosis of a human blood vessel.

BACKGROUND

Currently, physiological measurements and angiographic images are displayed on separate monitors or at least separate windows on a common monitor. As a result, medical personnel must attempt to determine what portion(s) of the angiographic image corresponds to the obtained physiological measurements while looking between separate monitors and/or different portions of a single monitor. In that regard, the black and white nature of angiographic images with "grayscale" contrast between the anatomy and radiopaque elements makes the radiopaque markers difficult to identify in many instances.

Further, the current focus of cardiovascular diagnostic techniques is to identify particular spots of the vasculature that may be suitable for treatment (e.g., stents, balloons, and/or other treatment techniques). Each of these locations is referred to as a focal stenosis. However, in some instances it is desirable to identify what is referred to as a diffuse stenosis. In particular, it is desirable to identify diffuse stenoses that extend over the length of the vessel such that when considered over a majority or the entire length of the diffuse stenosis presents as a clinically significant stenosis, but when considered over shorter, partial lengths of the diffuse stenosis may appear as innocuous or at least less problematic. By evaluating the effects of both focal stenoses and diffuse stenoses a more complete diagnosis of the patient can be made, which leads to more appropriate treatments and, therefore, better patient outcomes.

Aspects of the present disclosure, address these and other issues surrounding intravascular diagnostic techniques and treatment techniques. For example, in some instances the present disclosure is directed to the control and display of intravascular images augmented with co-registered focal and/or diffuse physiological measurements (pressure, flow, temperature, viscosity, etc.).

SUMMARY

Embodiments of the present disclosure are configured to assess the severity of a blockage in a vessel and, in particular, a stenosis in a blood vessel. In some particular embodiments, the devices, systems, and methods of the present disclosure are configured to provide visual depictions of vessel that allow assessment of the vessel and, in particular, any stenosis or lesion of the vessel.

In some embodiments, methods of evaluating a vessel of a patient are provided. The method includes obtaining intravascular data from an intravascular instrument positioned within a vessel of a patient while the intravascular instrument is moved longitudinally through the vessel from a first position to a second position; obtaining an angiographic image of the vessel while the intravascular instrument is moved longitudinally through the vessel; correlating the intravascular data from the intravascular instrument to locations on the angiographic image; and outputting an enhanced angiographic image of the vessel on a display, the enhanced angiographic image including the angiographic image overlaid with visualizations representing the intravascular data at the correlated locations.

In some instances, the first position is distal of at least one stenosis of the vessel and the second position is proximal of the at least one stenosis of the vessel such that moving the second instrument longitudinally through the vessel comprises a pullback. The intravascular data can include an intravascular image. For example, the intravascular image is at least one of an intravascular ultrasound (IVUS) image and an optical coherence tomography (OCT) image in some instances. The intravascular data can also include a pressure measurement. To that end, the visualizations can include a representation of a calculated pressure ratio. The intravascular data can also include a flow measurement. Accordingly, the visualizations can include a representation of a calculated flow ratio. In some instances, the angiographic image is at least one of a two dimensional angiographic image, a three dimensional angiographic image, and a computed tomography angiographic (CTA) image. The visualizations can include an intensity map based on changes in the intravascular data as the intravascular instrument is moved longitudinally through the vessel. For example, a first visual characteristic of the intensity map is associated with intravascular data above a threshold value and a second visual characteristic of the intensity map is associated with intravascular data below the threshold value. In that regard, the first visual characteristic can be a first color and the second visual characteristic can be a second color visually distinguishable from the first color. Systems for performing such methods are also provided.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
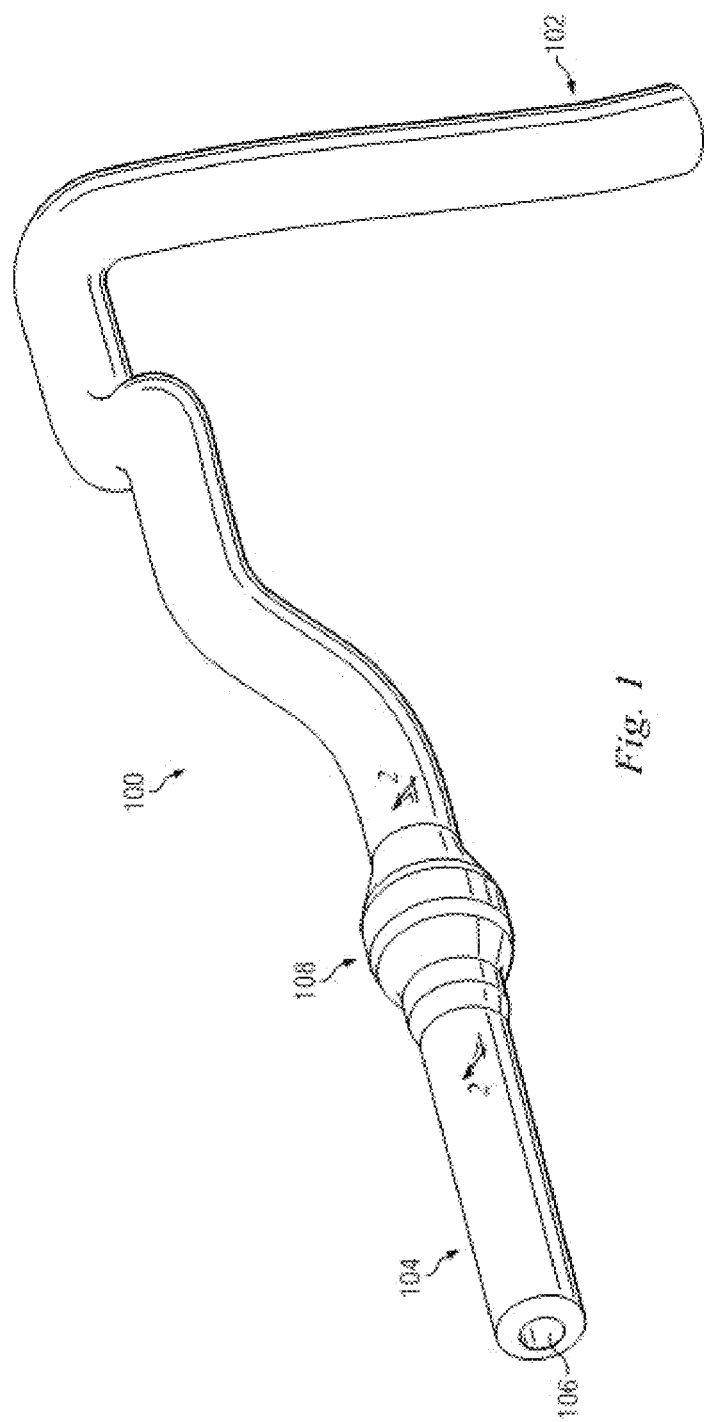
FIG. 1 is a diagrammatic perspective view of a vessel having a stenosis according to an embodiment of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

Figure 2:
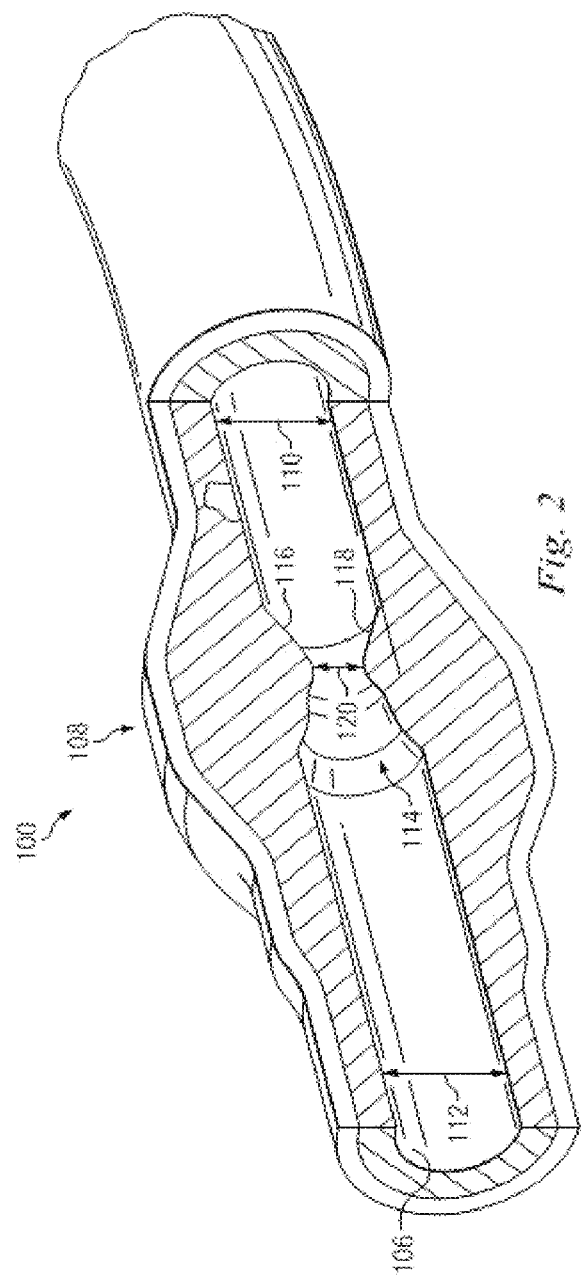
FIG. 2 is a diagrammatic, partial cross-sectional perspective view of a portion of the vessel of FIG. 1 taken along section line 2-2 of FIG. 1.

Referring to FIGS. 1 and 2, shown therein is a vessel 100 having a stenosis according to an embodiment of the present disclosure. In that regard, FIG. 1 is a diagrammatic perspective view of the vessel 100, while FIG. 2 is a partial cross-sectional perspective view of a portion of the vessel 100 taken along section line 2-2 of FIG. 1. Referring more specifically to FIG. 1, the vessel 100 includes a proximal portion 102 and a distal portion 104. A lumen 106 extends along the length of the vessel 100 between the proximal portion 102 and the distal portion 104. In that regard, the lumen 106 is configured to allow the flow of fluid through the vessel. In some instances, the vessel 100 is a blood vessel. In some particular instances, the vessel 100 is a coronary artery. In such instances, the lumen 106 is configured to facilitate the flow of blood through the vessel 100.

As shown, the vessel 100 includes a stenosis 108 between the proximal portion 102 and the distal portion 104. Stenosis 108 is generally representative of any blockage or other structural arrangement that results in a restriction to the flow of fluid through the lumen 106 of the vessel 100. Embodiments of the present disclosure are suitable for use in a wide variety of vascular applications, including without limitation coronary, peripheral (including but not limited to lower limb, carotid, and neurovascular), renal, and/or venous. Where the vessel 100 is a blood vessel, the stenosis 108 may be a result of plaque buildup, including without limitation plaque components such as fibrous, fibro-lipidic (fibro fatty), necrotic core, calcified (dense calcium), blood, fresh thrombus, and mature thrombus. Generally, the composition of the stenosis will depend on the type of vessel being evaluated. In that regard, it is understood that the concepts of the present disclosure are applicable to virtually any type of blockage or other narrowing of a vessel that results in decreased fluid flow.

Referring more particularly to FIG. 2, the lumen 106 of the vessel 100 has a diameter 110 proximal of the stenosis 108 and a diameter 112 distal of the stenosis. In some instances, the diameters 110 and 112 are substantially equal to one another. In that regard, the diameters 110 and 112 are intended to represent healthy portions, or at least healthier portions, of the lumen 106 in comparison to stenosis 108. Accordingly, these healthier portions of the lumen 106 are illustrated as having a substantially constant cylindrical profile and, as a result, the height or width of the lumen has been referred to as a diameter. However, it is understood that in many instances these portions of the lumen 106 will also have plaque buildup, a non-symmetric profile, and/or other irregularities, but to a lesser extent than stenosis 108 and, therefore, will not have a cylindrical profile. In such instances, the diameters 110 and 112 are understood to be representative of a relative size or cross-sectional area of the lumen and do not imply a circular cross-sectional profile.

As shown in FIG. 2, stenosis 108 includes plaque buildup 114 that narrows the lumen 106 of the vessel 100. In some instances, the plaque buildup 114 does not have a uniform or symmetrical profile, making angiographic evaluation of such a stenosis unreliable. In the illustrated embodiment, the plaque buildup 114 includes an upper portion 116 and an opposing lower portion 118. In that regard, the lower portion 118 has an increased thickness relative to the upper portion 116 that results in a non-symmetrical and non-uniform profile relative to the portions of the lumen proximal and distal of the stenosis 108. As shown, the plaque buildup 114 decreases the available space for fluid to flow through the lumen 106. In particular, the cross-sectional area of the lumen 106 is decreased by the plaque buildup 114. At the narrowest point between the upper and lower portions 116, 118 the lumen 106 has a height 120, which is representative of a reduced size or cross-sectional area relative to the diameters 110 and 112 proximal and distal of the stenosis 108. Note that the stenosis 108, including plaque buildup 114 is exemplary in nature and should be considered limiting in any way. In that regard, it is understood that the stenosis 108 has other shapes and/or compositions that limit the flow of fluid through the lumen 106 in other instances. While the vessel 100 is illustrated in FIGS. 1 and 2 as having a single stenosis 108 and the description of the embodiments below is primarily made in the context of a single stenosis, it is nevertheless understood that the devices, systems, and methods described herein have similar application for a vessel having multiple stenosis regions.

Figure 3:
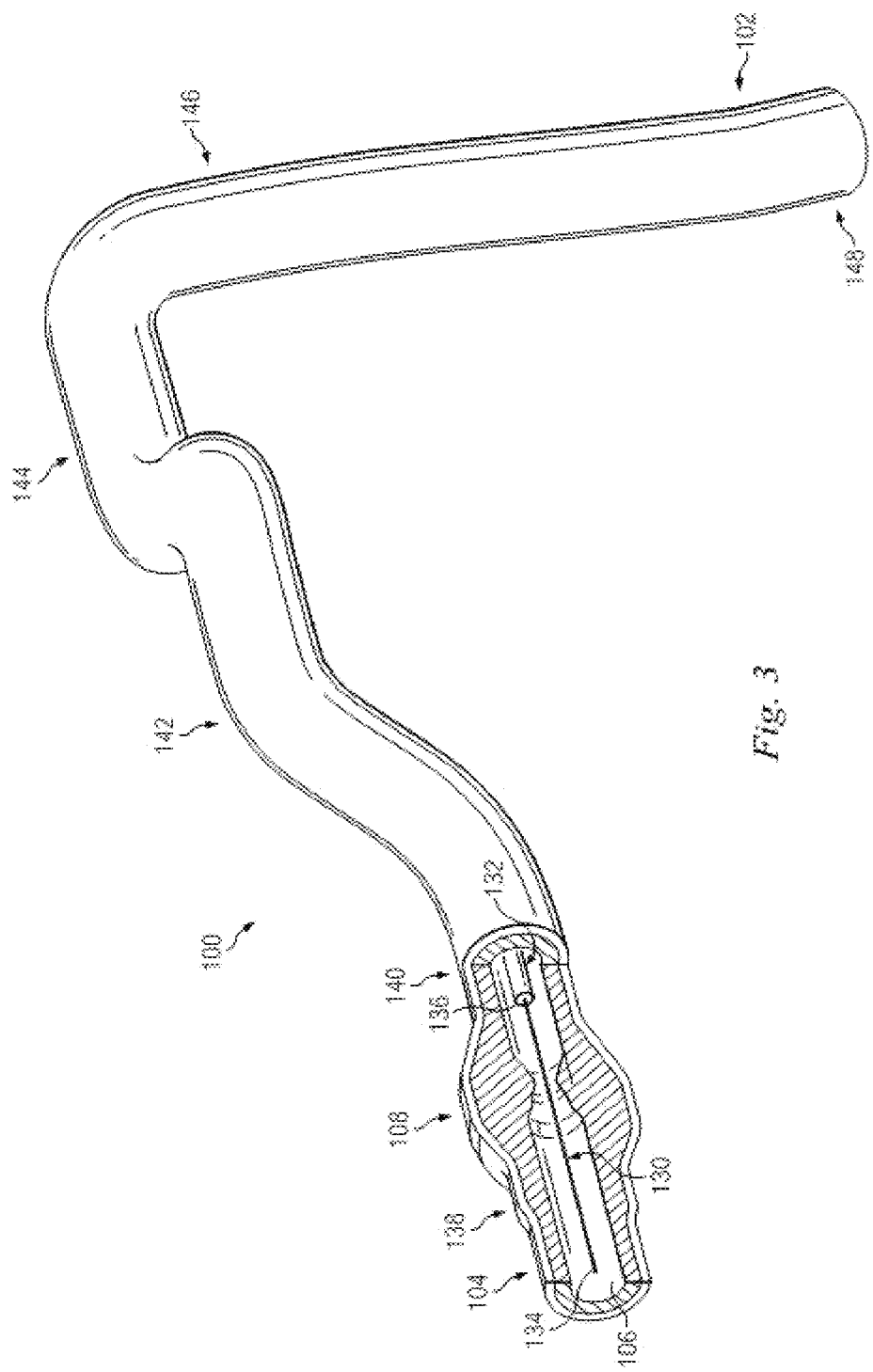
FIG. 3 is a diagrammatic, partial cross-sectional perspective view of the vessel of FIGS. 1 and 2 with instruments positioned therein according to an embodiment of the present disclosure.

Referring now to FIG. 3, the vessel 100 is shown with instruments 130 and 132 positioned therein according to an embodiment of the present disclosure. In general, instruments 130 and 132 may be any form of device, instrument, or probe sized and shaped to be positioned within a vessel. In the illustrated embodiment, instrument 130 is generally representative of a guide wire, while instrument 132 is generally representative of a catheter. In that regard, instrument 130 extends through a central lumen of instrument 132. However, in other embodiments, the instruments 130 and 132 take other forms. In that regard, the instruments 130 and 132 are of similar form in some embodiments. For example, in some instances, both instruments 130 and 132 are guide wires. In other instances, both instruments 130 and 132 are catheters. On the other hand, the instruments 130 and 132 are of different form in some embodiments, such as the illustrated embodiment, where one of the instruments is a catheter and the other is a guide wire. Further, in some instances, the instruments 130 and 132 are disposed coaxial with one another, as shown in the illustrated embodiment of FIG. 3. In other instances, one of the instruments extends through an off-center lumen of the other instrument. In yet other instances, the instruments 130 and 132 extend side-by-side. In some particular embodiments, at least one of the instruments is as a rapid-exchange device, such as a rapid-exchange catheter. In such embodiments, the other instrument is a buddy wire or other device configured to facilitate the introduction and removal of the rapid-exchange device. Further still, in other instances, instead of two separate instruments 130 and 132 a single instrument is utilized. In some embodiments, the single instrument incorporates aspects of the functionalities (e.g., data acquisition) of both instruments 130 and 132.

Instrument 130 is configured to obtain diagnostic information about the vessel 100. In that regard, the instrument 130 includes one or more sensors, transducers, and/or other monitoring elements configured to obtain the diagnostic information about the vessel. The diagnostic information includes one or more of pressure, flow (velocity), images (including images obtained using ultrasound (e.g., IVUS), OCT, thermal, and/or other imaging techniques), temperature, and/or combinations thereof. The one or more sensors, transducers, and/or other monitoring elements are positioned adjacent a distal portion of the instrument 130 in some instances. In that regard, the one or more sensors, transducers, and/or other monitoring elements are positioned less than 30 cm, less than 10 cm, less than 5 cm, less than 3 cm, less than 2 cm, and/or less than 1 cm from a distal tip 134 of the instrument 130 in some instances. In some instances, at least one of the one or more sensors, transducers, and/or other monitoring elements is positioned at the distal tip of the instrument 130.

The instrument 130 includes at least one element configured to monitor pressure within the vessel 100. The pressure monitoring element can take the form a piezo-resistive pressure sensor, a piezo-electric pressure sensor, a capacitive pressure sensor, an electromagnetic pressure sensor, a fluid column (the fluid column being in communication with a fluid column sensor that is separate from the instrument and/or positioned at a portion of the instrument proximal of the fluid column), an optical pressure sensor, and/or combinations thereof. In some instances, one or more features of the pressure monitoring element are implemented as a solid-state component manufactured using semiconductor and/or other suitable manufacturing techniques. Examples of commercially available guide wire products that include suitable pressure monitoring elements include, without limitation, the PrimeWire PRESTIGE® pressure guide wire, the PrimeWire® pressure guide wire, and the ComboWire® XT pressure and flow guide wire, each available from Volcano Corporation, as well as the PressureWire™ Certus guide wire and the PressureWire™ Aeris guide wire, each available from St. Jude Medical, Inc. Generally, the instrument 130 is sized such that it can be positioned through the stenosis 108 without significantly impacting fluid flow across the stenosis, which would impact the distal pressure reading. Accordingly, in some instances the instrument 130 has an outer diameter of 0.018" or less. In some embodiments, the instrument 130 has an outer diameter of 0.014" or less.

Instrument 132 is also configured to obtain diagnostic information about the vessel 100. In some instances, instrument 132 is configured to obtain the same diagnostic information as instrument 130. In other instances, instrument 132 is configured to obtain different diagnostic information than instrument 130, which may include additional diagnostic information, less diagnostic information, and/or alternative diagnostic information. The diagnostic information obtained by instrument 132 includes one or more of pressure, flow (velocity), images (including images obtained using ultrasound (e.g., IVUS), OCT, thermal, and/or other imaging techniques), temperature, and/or combinations thereof. Instrument 132 includes one or more sensors, transducers, and/or other monitoring elements configured to obtain this diagnostic information. In that regard, the one or more sensors, transducers, and/or other monitoring elements are positioned adjacent a distal portion of the instrument 132 in some instances. In that regard, the one or more sensors, transducers, and/or other monitoring elements are positioned less than 30 cm, less than 10 cm, less than 5 cm, less than 3 cm, less than 2 cm, and/or less than 1 cm from a distal tip 136 of the instrument 132 in some instances. In some instances, at least one of the one or more sensors, transducers, and/or other monitoring elements is positioned at the distal tip of the instrument 132.

Similar to instrument 130, instrument 132 also includes at least one element configured to monitor pressure within the vessel 100. The pressure monitoring element can take the form a piezo-resistive pressure sensor, a piezo-electric pressure sensor, a capacitive pressure sensor, an electromagnetic pressure sensor, a fluid column (the fluid column being in communication with a fluid column sensor that is separate from the instrument and/or positioned at a portion of the instrument proximal of the fluid column), an optical pressure sensor, and/or combinations thereof. In some instances, one or more features of the pressure monitoring element are implemented as a solid-state component manufactured using semiconductor and/or other suitable manufacturing techniques. Currently available catheter products suitable for use with one or more of Siemens AXIOM Sensis, Mennen Horizon XVu, and Philips Xper IM Physiomonitoring 5 and include pressure monitoring elements can be utilized for instrument 132 in some instances.

In accordance with aspects of the present disclosure, at least one of the instruments 130 and 132 is configured to monitor a pressure within the vessel 100 distal of the stenosis 108 and at least one of the instruments 130 and 132 is configured to monitor a pressure within the vessel proximal of the stenosis. In that regard, the instruments 130, 132 are sized and shaped to allow positioning of the at least one element configured to monitor pressure within the vessel 100 to be positioned proximal and/or distal of the stenosis 108 as necessary based on the configuration of the devices. In that regard, FIG. 3 illustrates a position 138 suitable for measuring pressure distal of the stenosis 108. In that regard, the position 138 is less than 5 cm, less than 3 cm, less than 2 cm, less than 1 cm, less than 5 mm, and/or less than 2.5 mm from the distal end of the stenosis 108 (as shown in FIG. 2) in some instances. FIG. 3 also illustrates a plurality of suitable positions for measuring pressure proximal of the stenosis 108. In that regard, positions 140, 142, 144, 146, and 148 each represent a position that is suitable for monitoring the pressure proximal of the stenosis in some instances. In that regard, the positions 140, 142, 144, 146, and 148 are positioned at varying distances from the proximal end of the stenosis 108 ranging from more than 20 cm down to about 5 mm or less. Generally, the proximal pressure measurement will be spaced from the proximal end of the stenosis. Accordingly, in some instances, the proximal pressure measurement is taken at a distance equal to or greater than an inner diameter of the lumen of the vessel from the proximal end of the stenosis. In the context of coronary artery pressure measurements, the proximal pressure measurement is generally taken at a position proximal of the stenosis and distal of the aorta, within a proximal portion of the vessel. However, in some particular instances of coronary artery pressure measurements, the proximal pressure measurement is taken from a location inside the aorta. In other instances, the proximal pressure measurement is taken at the root or ostium of the coronary artery.

In some embodiments, at least one of the instruments 130 and 132 is configured to monitor pressure within the vessel 100 while being moved through the lumen 106. In some instances, instrument 130 is configured to be moved through the lumen 106 and across the stenosis 108. In that regard, the instrument 130 is positioned distal of the stenosis 108 and moved proximally (i.e., pulled back) across the stenosis to a position proximal of the stenosis in some instances. In other instances, the instrument 130 is positioned proximal of the stenosis 108 and moved distally across the stenosis to a position distal of the stenosis. Movement of the instrument 130, either proximally or distally, is controlled manually by medical personnel (e.g., hand of a surgeon) in some embodiments. In other embodiments, movement of the instrument 130, either proximally or distally, is controlled automatically by a movement control device (e.g., a pullback device, such as the Trak Back® II Device available from Volcano Corporation). In that regard, the movement control device controls the movement of the instrument 130 at a selectable and known speed (e.g., 2.0 mm/s, 1.0 mm/s, 0.5 mm/s, 0.2 mm/s, etc.) in some instances. Movement of the instrument 130 through the vessel is continuous for each pullback or push through, in some instances. In other instances, the instrument 130 is moved step-wise through the vessel (i.e., repeatedly moved a fixed amount of distance and/or a fixed amount of time). Some aspects of the visual depictions discussed below are particularly suited for embodiments where at least one of the instruments 130 and 132 is moved through the lumen 106. Further, in some particular instances, aspects of the visual depictions discussed below are particularly suited for embodiments where a single instrument is moved through the lumen 106, with or without the presence of a second instrument.

In some instances, use of a single instrument has a benefit in that it avoids issues associated with variations in pressure measurements of one instrument relative to another over time, which is commonly referred to as drift. In that regard, a major source of drift in traditional Fractional Flow Reserve (FFR) measurements is divergence in the pressure reading of a guidewire relative to the pressure reading of a guide catheter. In that regard, because FFR is calculated as the ratio of the pressure measurement obtained by the guidewire to the pressure measurement obtained by the catheter, this divergence has an impact on the resulting FFR value. In contrast, where a single instrument is utilized to obtain pressure measurements as it is moved through the vessel, drift is negligible or non-existent. For example, in some instances, the single instrument is utilized to obtain relative changes in pressures as it is moved through the vessel such that the time period between pressure measurements is short enough to prevent any impact from any changes in pressure sensitivity of the instrument (e.g., less than 500 ms, less than 100 ms, less than 50 ms, less than 10 ms, less than 5 ms, less than 1 ms, or otherwise).

Figure 4:
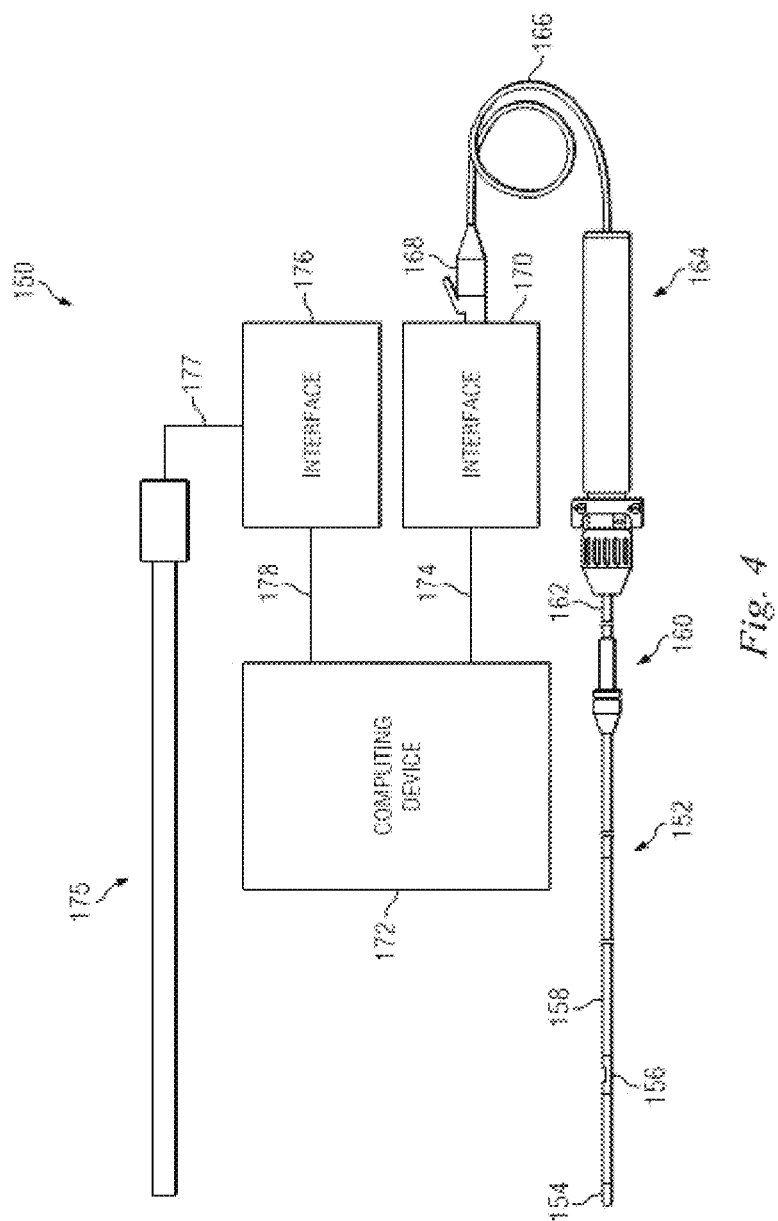
FIG. 4 is a diagrammatic, schematic view of a system according to an embodiment of the present disclosure.

Referring now to FIG. 4, shown therein is a system 150 according to an embodiment of the present disclosure. In that regard, FIG. 4 is a diagrammatic, schematic view of the system 150. As shown, the system 150 includes an instrument 152. In that regard, in some instances instrument 152 is suitable for use as at least one of instruments 130 and 132 discussed above. Accordingly, in some instances the instrument 152 includes features similar to those discussed above with respect to instruments 130 and 132 in some instances. In the illustrated embodiment, the instrument 152 is a guide wire having a distal portion 154 and a housing 156 positioned adjacent the distal portion. In that regard, the housing 156 is spaced approximately 3 cm from a distal tip of the instrument 152. The housing 156 is configured to house one or more sensors, transducers, and/or other monitoring elements configured to obtain the diagnostic information about the vessel. In the illustrated embodiment, the housing 156 contains at least a pressure sensor configured to monitor a pressure within a lumen in which the instrument 152 is positioned. A shaft 158 extends proximally from the housing 156. A torque device 160 is positioned over and coupled to a proximal portion of the shaft 158. A proximal end portion 162 of the instrument 152 is coupled to a connector 164. A cable 166 extends from connector 164 to a connector 168. In some instances, connector 168 is configured to be plugged into an interface 170. In that regard, interface 170 is a patient interface module (PIM) in some instances. In some instances, the cable 166 is replaced with a wireless connection. In that regard, it is understood that various communication pathways between the instrument 152 and the interface 170 may be utilized, including physical connections (including electrical, optical, and/or fluid connections), wireless connections, and/or combinations thereof.

The interface 170 is communicatively coupled to a computing device 172 via a connection 174. Computing device 172 is generally representative of any device suitable for performing the processing and analysis techniques discussed within the present disclosure. In some embodiments, the computing device 172 includes a processor, random access memory, and a storage medium. In that regard, in some particular instances the computing device 172 is programmed to execute steps associated with the data acquisition and analysis described herein. Accordingly, it is understood that any steps related to data acquisition, data processing, instrument control, and/or other processing or control aspects of the present disclosure may be implemented by the computing device using corresponding instructions stored on or in a non-transitory computer readable medium accessible by the computing device. In some instances, the computing device 172 is a console device. In some particular instances, the computing device 172 is similar to the s5™ Imaging System or the s5i™ Imaging System, each available from Volcano Corporation. In some instances, the computing device 172 is portable (e.g., handheld, on a rolling cart, etc.). Further, it is understood that in some instances the computing device 172 comprises a plurality of computing devices. In that regard, it is particularly understood that the different processing and/or control aspects of the present disclosure may be implemented separately or within predefined groupings using a plurality of computing devices. Any divisions and/or combinations of the processing and/or control aspects described below across multiple computing devices are within the scope of the present disclosure.

Together, connector 164, cable 166, connector 168, interface 170, and connection 174 facilitate communication between the one or more sensors, transducers, and/or other monitoring elements of the instrument 152 and the computing device 172. However, this communication pathway is exemplary in nature and should not be considered limiting in any way. In that regard, it is understood that any communication pathway between the instrument 152 and the computing device 172 may be utilized, including physical connections (including electrical, optical, and/or fluid connections), wireless connections, and/or combinations thereof. In that regard, it is understood that the connection 174 is wireless in some instances. In some instances, the connection 174 includes a communication link over a network (e.g., intranet, internet, telecommunications network, and/or other network). In that regard, it is understood that the computing device 172 is positioned remote from an operating area where the instrument 152 is being used in some instances. Having the connection 174 include a connection over a network can facilitate communication between the instrument 152 and the remote computing device 172 regardless of whether the computing device is in an adjacent room, an adjacent building, or in a different state/country. Further, it is understood that the communication pathway between the instrument 152 and the computing device 172 is a secure connection in some instances. Further still, it is understood that, in some instances, the data communicated over one or more portions of the communication pathway between the instrument 152 and the computing device 172 is encrypted.

The system 150 also includes an instrument 175. In that regard, in some instances instrument 175 is suitable for use as at least one of instruments 130 and 132 discussed above. Accordingly, in some instances the instrument 175 includes features similar to those discussed above with respect to instruments 130 and 132 in some instances. In the illustrated embodiment, the instrument 175 is a catheter-type device. In that regard, the instrument 175 includes one or more sensors, transducers, and/or other monitoring elements adjacent a distal portion of the instrument configured to obtain the diagnostic information about the vessel. In the illustrated embodiment, the instrument 175 includes a pressure sensor configured to monitor a pressure within a lumen in which the instrument 175 is positioned. The instrument 175 is in communication with an interface 176 via connection 177. In some instances, interface 176 is a hemodynamic monitoring system or other control device, such as Siemens AXIOM Sensis, Mennen Horizon XVu, and Philips Xper IM Physiomonitoring 5. In one particular embodiment, instrument 175 is a pressure-sensing catheter that includes fluid column extending along its length. In such an embodiment, interface 176 includes a hemostasis valve fluidly coupled to the fluid column of the catheter, a manifold fluidly coupled to the hemostasis valve, and tubing extending between the components as necessary to fluidly couple the components. In that regard, the fluid column of the catheter is in fluid communication with a pressure sensor via the valve, manifold, and tubing. In some instances, the pressure sensor is part of interface 176. In other instances, the pressure sensor is a separate component positioned between the instrument 175 and the interface 176. The interface 176 is communicatively coupled to the computing device 172 via a connection 178.

Similar to the connections between instrument 152 and the computing device 172, interface 176 and connections 177 and 178 facilitate communication between the one or more sensors, transducers, and/or other monitoring elements of the instrument 175 and the computing device 172. However, this communication pathway is exemplary in nature and should not be considered limiting in any way. In that regard, it is understood that any communication pathway between the instrument 175 and the computing device 172 may be utilized, including physical connections (including electrical, optical, and/or fluid connections), wireless connections, and/or combinations thereof. In that regard, it is understood that the connection 178 is wireless in some instances. In some instances, the connection 178 includes a communication link over a network (e.g., intranet, interne, telecommunications network, and/or other network). In that regard, it is understood that the computing device 172 is positioned remote from an operating area where the instrument 175 is being used in some instances. Having the connection 178 include a connection over a network can facilitate communication between the instrument 175 and the remote computing device 172 regardless of whether the computing device is in an adjacent room, an adjacent building, or in a different state/country. Further, it is understood that the communication pathway between the instrument 175 and the computing device 172 is a secure connection in some instances. Further still, it is understood that, in some instances, the data communicated over one or more portions of the communication pathway between the instrument 175 and the computing device 172 is encrypted.

It is understood that one or more components of the system 150 are not included, are implemented in a different arrangement/order, and/or are replaced with an alternative device/mechanism in other embodiments of the present disclosure. For example, in some instances, the system 150 does not include interface 170 and/or interface 176. In such instances, the connector 168 (or other similar connector in communication with instrument 152 or instrument 175) may plug into a port associated with computing device 172. Alternatively, the instruments 152, 175 may communicate wirelessly with the computing device 172. Generally speaking, the communication pathway between either or both of the instruments 152, 175 and the computing device 172 may have no intermediate nodes (i.e., a direct connection), one intermediate node between the instrument and the computing device, or a plurality of intermediate nodes between the instrument and the computing device.

Diagnostic information within a vasculature of interest can be obtained using one or more of instruments 130, 132, 152, and 175. For example, diagnostic information is obtained for one or more coronaries arteries, peripheral arteries, cerebrovascular vessels, etc. The diagnostic information can include pressure-related values, flow-related values, etc. Pressure-related values can include FFR, Pd/Pa (e.g., a ratio of the pressure distal to a lesion to the pressure proximal to the lesion), iFR (e.g., a pressure ratio value calculated using a diagnostic window relative to a distance as a first instrument is moved through a vessel relative to a second instrument, including across at least one stenosis of the vessel), etc. Flow-related values can include coronary flow reserve or CFR (e.g., maximum increase in blood flow through the coronary arteries above the normal resting volume), basal stenosis resistance index (BSR), etc.

In some embodiments, the diagnostic information can include angiographic images and/or other two-dimensional or three-dimensional depictions of a patient's vasculature. The diagnostic information and/or data obtained by instruments 130, 132, 152, and/or 175 are correlated or co-registered to angiographic image(s) and/or other two-dimensional or three-dimensional depictions of a patient's vasculature. In some instances, the location of the intravascular instrument is depicted on the angiographic images. For example, identifiable markers of the intravascular instrument, such as radiopaque markers, can be visually depicted on the angiographic image to illustrate the location of the markers and, thereby, the intravascular instrument.

Figure 5:
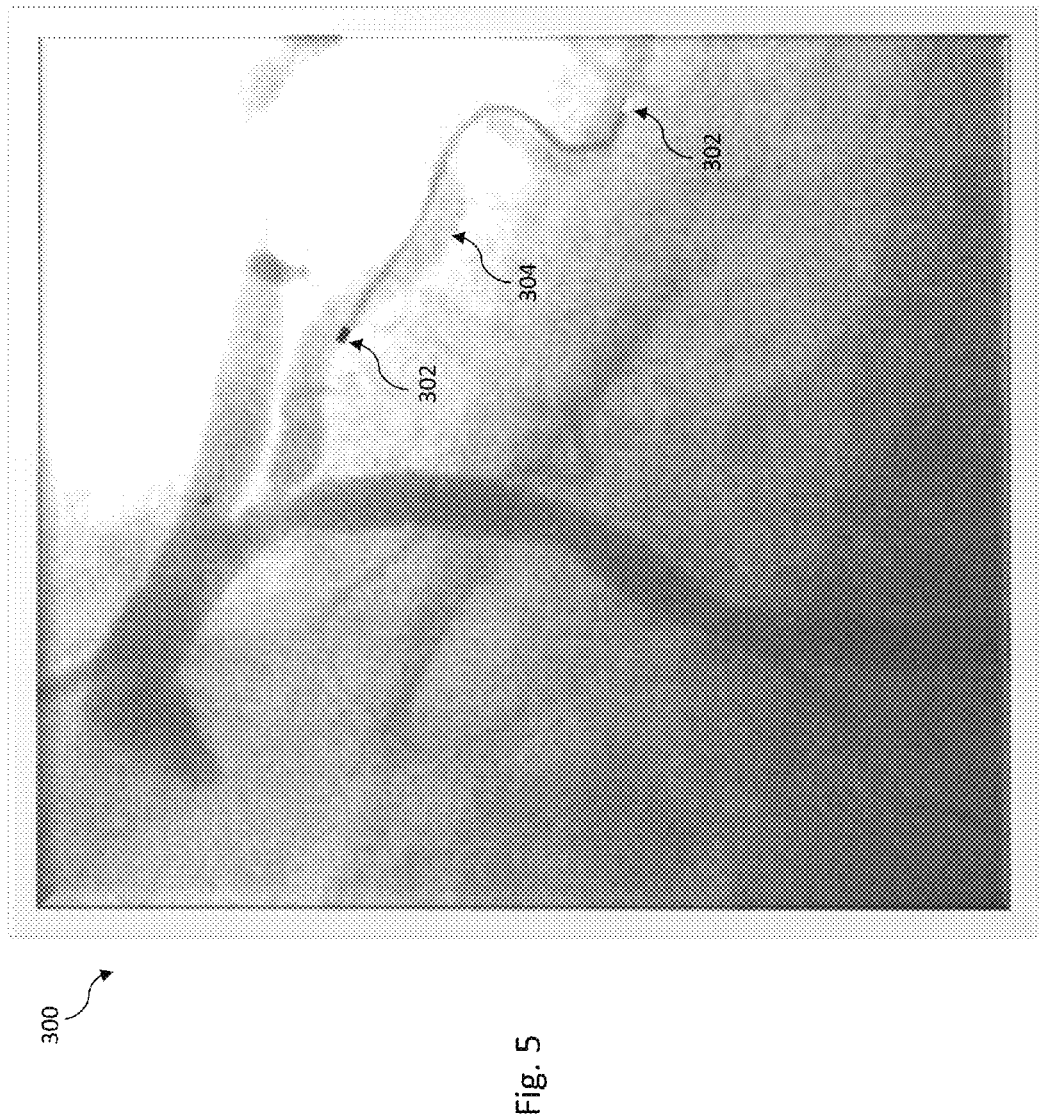
FIG. 5 is an enhanced angiographic image of a vessel according to an embodiment of the present disclosure.
Figure 6:
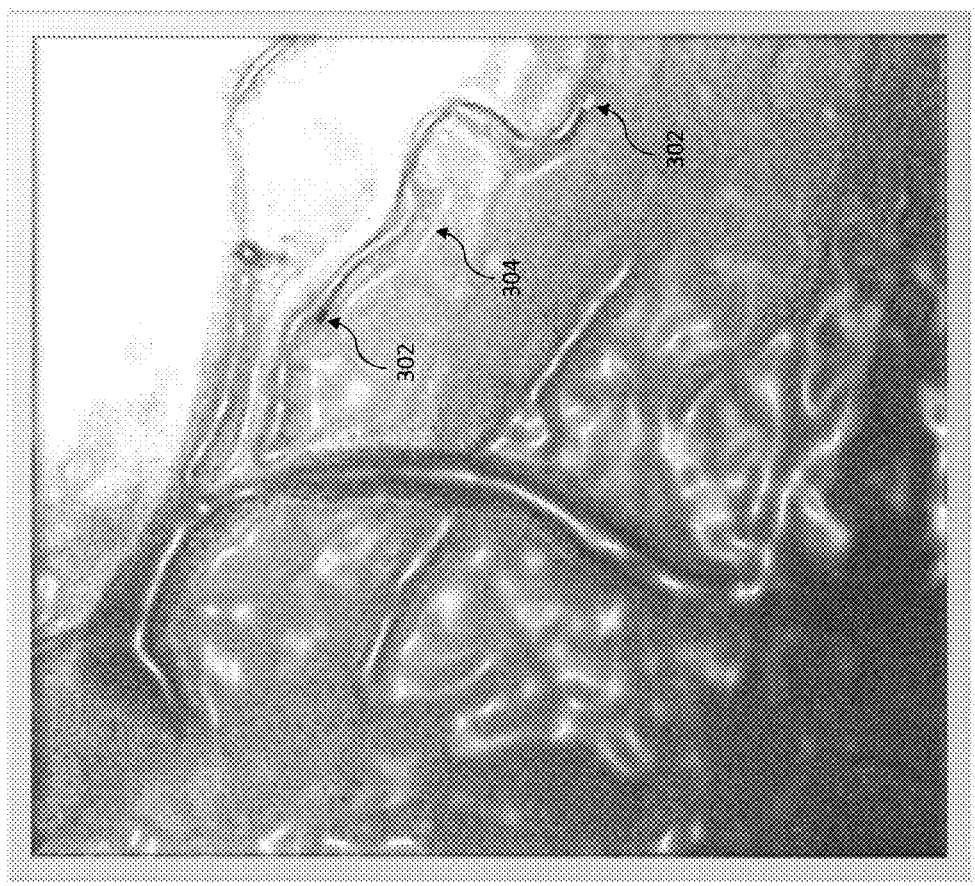
FIG. 6 is an enhanced angiographic image of a vessel according to an embodiment of the present disclosure.

In some implementations, the radiopaque elements of an intravascular instrument are algorithmically located, differentiated, and enhanced such that the radiopaque elements of the intravascular device are more easily visible in the angiographic display. For example, in some instances the radiopaque elements are displayed in a color (e.g., red, blue, yellow, green, etc.) that contrasts to the standard grayscale of the angiographic image display. FIG. 5 shows a representative display where an angiographic image 300 is shown with markers 302 of an intravascular instrument positioned within a vessel 304 visually accentuated. In some implementations, the angiographic image 300 is enhanced along with algorithmically locating, differentiating, and enhancing the radiopaque elements of the intravascular device. For example, in some instances the angiographic image 300 is filtered, processed, and/or otherwise treated to enhance the contrast between various portions of the anatomy and intravascular device(s) displayed in the angiographic image. This allows a user to more easily identify the location of the intravascular device within the vasculature and, therefore, the corresponding portions of the vasculature relevant for physiological measurements obtained with the intravascular device. FIG. 6 shows an angiographic image 310 after such enhancement treatments to the angiographic image 300 of FIG. 5.

Figure 7:
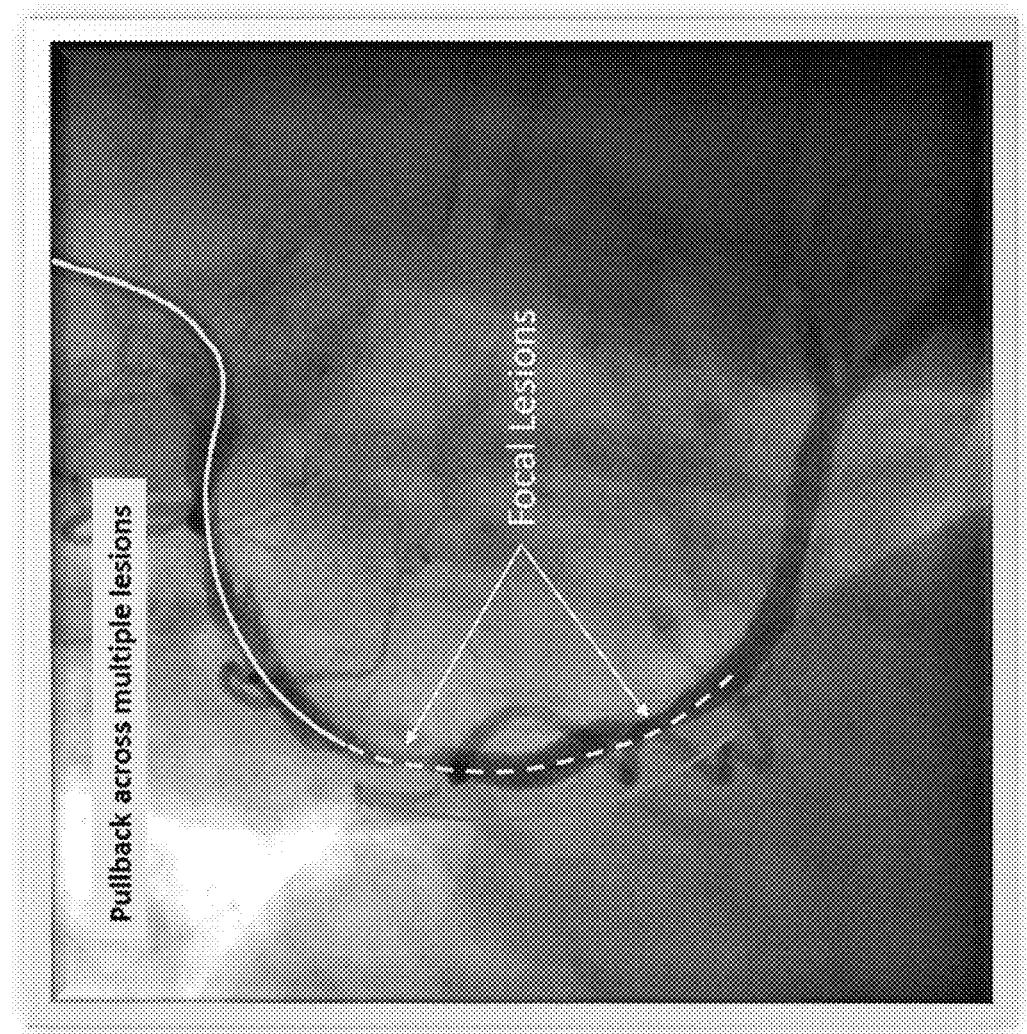
FIG. 7 is an enhanced angiographic image of a vessel according to an embodiment of the present disclosure.
Figure 8:
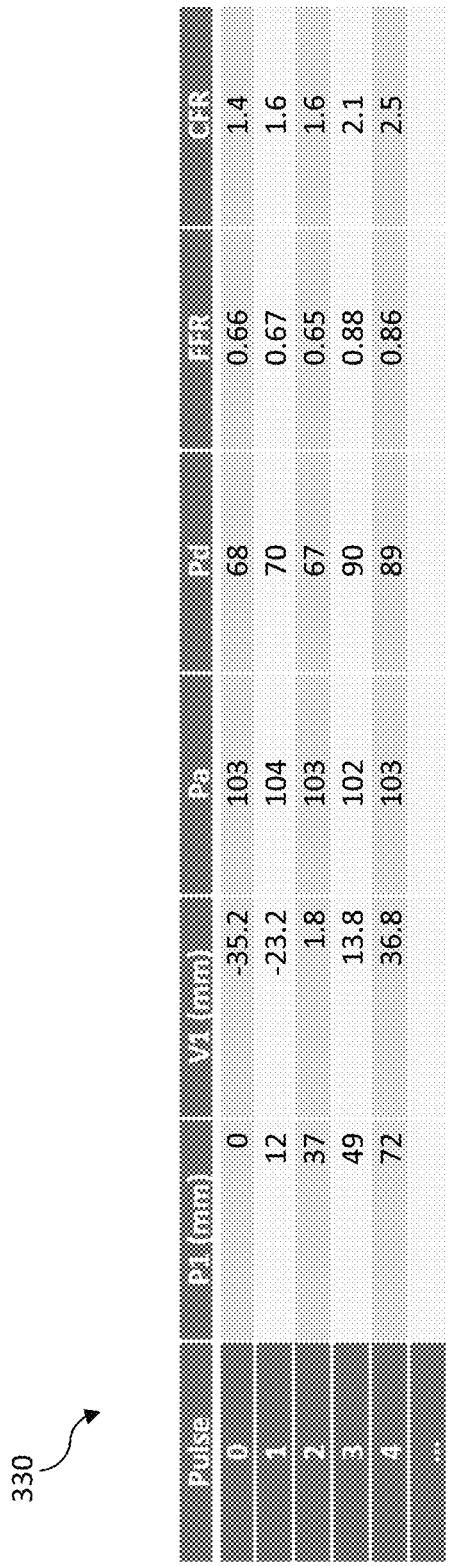
FIG. 8 is a chart of intravascular information according to an embodiment of the present disclosure.

In some instances, the physiological information is correlated or co-registered to the angiographic image(s) as a portion of the intravascular instrument is moved through the vasculature. For example, FIG. 7 shows an angiographic image 320 illustrating a pathway of an intravascular device being moved through a vessel having multiple focal lesions. To facilitate correlation/co-registration of the intravascular data with the angiographic image, in some implementations the following information is obtained and recorded at least once every heartbeat (or other regular interval), while moving the intravascular instrument through the vessel: pulse number; physiology measurement(s); angiographic image (and orientation); location on image of radiopaque elements; and/or vascular location of measurement—relative to start/zero position. The information may be maintained in a chart or other data structure for subsequent use and/or processing. For example, FIG. 8 shows a representative chart 330. In some embodiments, the movement of the intravascular device is tracked with a resolution of about 1 mm per heart beat. The relative amount of movement of the intravascular device to the vasculature can be monitored using a linear encoder at the proximal portion of the device (e.g., outside of the patient). In other instances, the relative amount of movement is determined by image processing of the angiographic images.

Co-registration of the location of the intravascular instrument (and corresponding data acquisitions) with the angiographic image(s) can be completed using techniques disclosed in U.S. Pat. No. 7,930,014, titled "VASCULAR IMAGE CO-REGISTRATION," which is hereby incorporated by reference in its entirety, based on the known pullback speed/distance, based on a known starting point, based on a known ending point, and/or combinations thereof. In some embodiments, diagnostic information and/or data is correlated to vessel images using techniques similar to those described in one or more of U.S. Pat. No. 8,290,228, titled "LOCATION-SENSITIVE CURSOR CONTROL AND ITS USE FOR VESSEL ANALYSIS," U.S. patent application Ser. No. 12/666,879, filed Dec. 28, 2009 and titled "AUTOMATIC QUANTITATIVE VESSEL ANALYSIS," PCT Patent Application No. PCT/IL2008/000316, filed on Mar. 9, 2008 and titled "IMAGING AND TOOLS FOR USE WITH MOVING ORGANS," U.S. patent application Ser. No. 12/075,244, filed Mar. 10, 2008 and titled "IMAGING FOR USE WITH MOVING ORGANS," U.S. patent application Ser. No. 12/075,214, filed Mar. 10, 2008 and entitled "TOOLS FOR USE WITH MOVING ORGANS," and U.S. patent application Ser. No. 12/075,252, filed Mar. 10, 2008 and titled "IMAGING AND TOOLS FOR USE WITH MOVING ORGANS," each of which is hereby incorporated by reference in its entirety. In some embodiments, co-registration and/or correlation can be completed as described in U.S. Provisional Patent Application No. 61/856,509, filed Jul. 19, 2013 and titled "DEVICES, SYSTEMS, AND METHODS FOR ASSESSMENT OF VESSELS," which is hereby incorporated by reference in its entirety.

Figure 9:
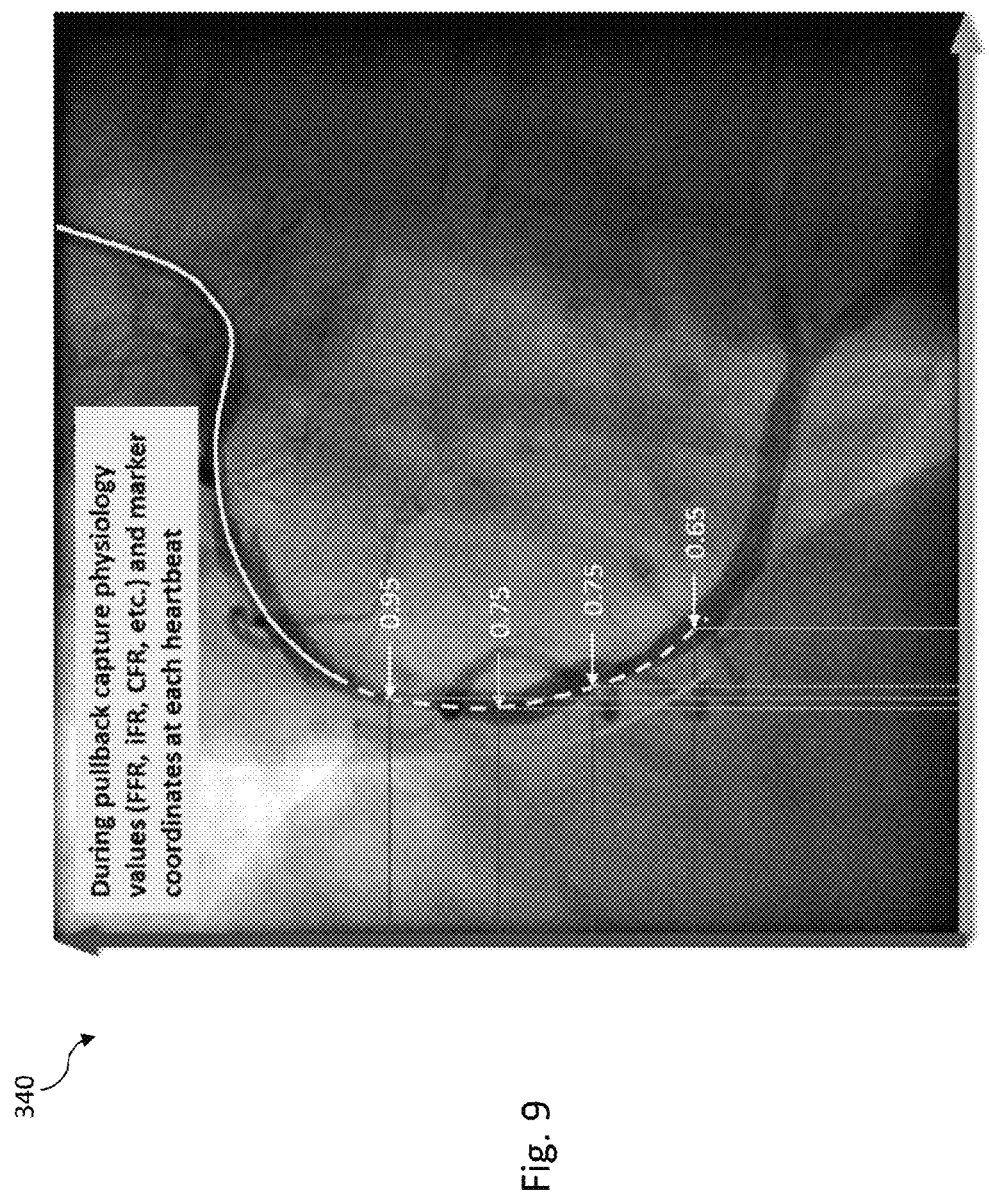
FIG. 9 is an enhanced angiographic image of a vessel according to an embodiment of the present disclosure.
Figure 10:
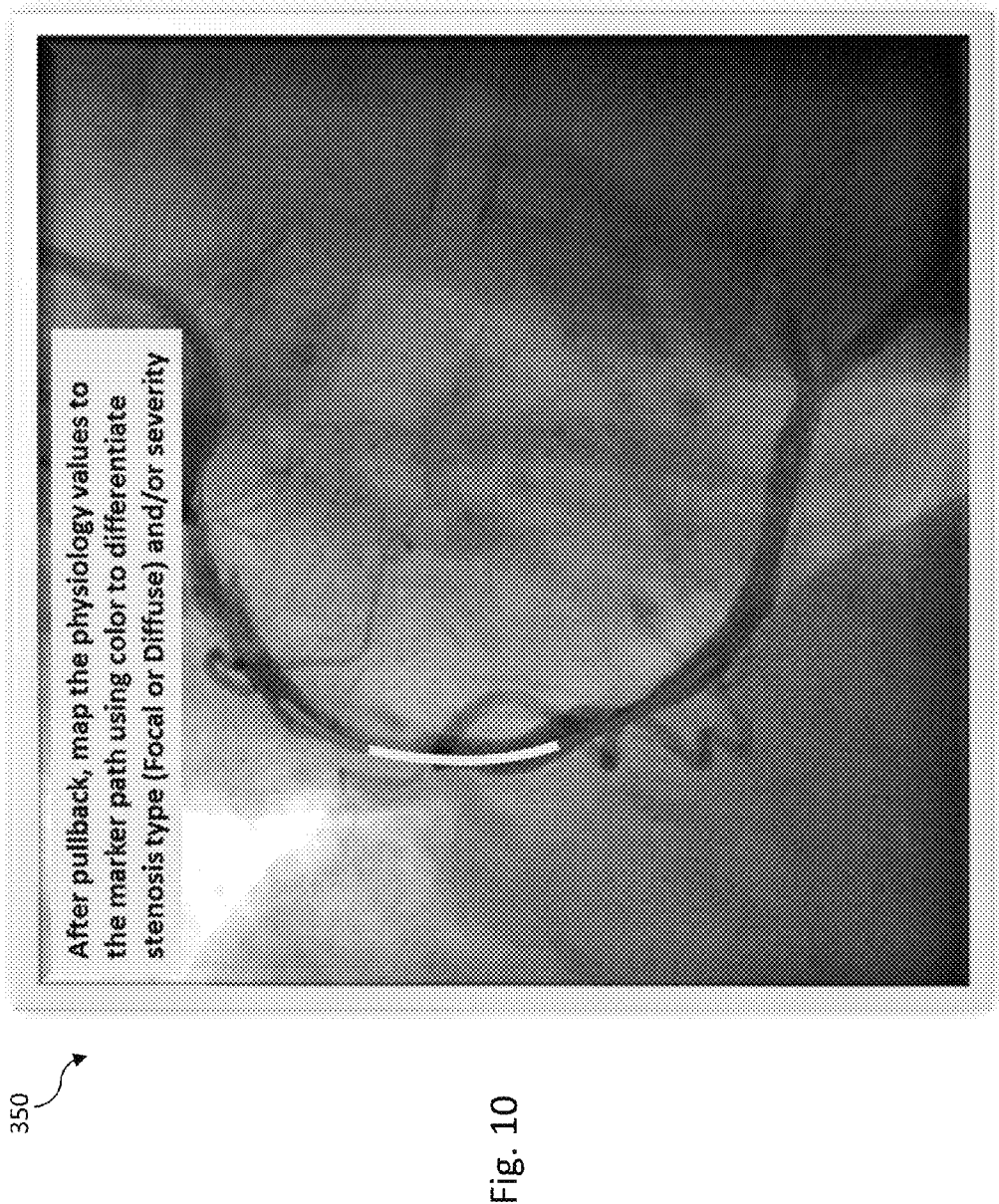
FIG. 10 is an enhanced angiographic image of a vessel according to an embodiment of the present disclosure.

Referring now to FIG. 9, shown therein is an enhanced angiographic image 340 of a vessel based on intravascular measurements according to an embodiment of the present disclosure. As shown, the intravascular physiological measurements are overlaid onto the angiographic image based on the locations of the marker(s) of the intravascular instrument when the intravascular data is obtained by the intravascular instrument. As shown in FIG. 9, the angiographic images of vessels can be annotated with one or more visualizations configured to assist in identifying one or more lesions and/or stenoses, and/or assess the severity thereof. The visualizations are based on the physiology values obtained from an instrument (e.g., instrument 130) as the instrument is positioned within and/or moved through the vessel. For example, FIG. 9 illustrates pressure ratio calculations (such as FFR or iFR) at different points along the length of the vessel. The vessel can be colorized and/or otherwise visualized using a heat map that illustrates changes in pressure measurements obtained as the instrument is moved through the vessel. For example, FIG. 10 illustrates an enhanced angiographic image 350 representing the same pressure ratio calculations as FIG. 9, but using a heat map approach where different colors provide an indication of the corresponding pressure ratio. In this manner, the colors can provide an indication of the severity of a lesion and whether it is a focal or diffuse lesion.

In some instances the pressure measurements shown in the heat map are representative of a pressure differential between a fixed location within the vessel and the moving position of the instrument as the instrument is moved through the vessel. For example, in some instances a proximal pressure measurement is obtained at a fixed location within the vessel while the instrument is pulled back through the vessel from a first position distal of the position where the proximal pressure measurement is obtained to a second position more proximal than the first position (i.e., closer the fixed position of the distal pressure measurement).

For clarity in understanding the concepts of the present disclosure, this arrangement of having one instrument pulled back while another is stationary will be utilized to describe many of the embodiments of the present disclosure. However, it is understood that the concepts are equally applicable to other arrangements. For example, in some instances, the instrument is pushed through the vessel from a first position distal of the proximal pressure measurement location to a second position further distal (i.e., further away from the fixed position of the proximal pressure measurement). In other instances, a distal pressure measurement is obtained at a fixed location within the vessel and the instrument is pulled back through the vessel from a first position proximal of the fixed location of the distal pressure measurement to a second position more proximal than the first position (i.e., further away from the fixed position of the distal pressure measurement). In still other instances, a distal pressure measurement is obtained at a fixed location within the vessel and the instrument is pushed through the vessel from a first position proximal of the fixed location of the distal pressure measurement to a second position less proximal than the first position (i.e., closer the fixed position of the distal pressure measurement).

The pressure differential between the two pressure measurements within the vessel (e.g., a fixed location pressure measurement and a moving pressure measurement) is calculated as a ratio of the two pressure measurements (e.g., the moving pressure measurement divided by the fixed location pressure measurement), in some instances. In some instances, the pressure differential is calculated for each heartbeat cycle of the patient. In that regard, the calculated pressure differential is the average pressure differential across a heartbeat cycle in some embodiments. For example, in some instances where a hyperemic agent is applied to the patient, the average pressure differential across the heartbeat cycle is utilized to calculate the pressure differential. In other embodiments, only a portion of the heartbeat cycle is utilized to calculate the pressure differential. The pressure differential is an average over the portion or diagnostic window of the heartbeat cycle, in some instances. In that regard, in some embodiments a diagnostic window is selected using one or more of the techniques described in U.S. patent application Ser. No. 13/460,296, filed Apr. 30, 2012 and titled "DEVICES, SYSTEMS, AND METHODS FOR ASSESSING A VESSEL," which is hereby incorporated by reference in its entirety. As discussed therein, the diagnostic windows and associated techniques are particularly suitable for use without application of a hyperemic agent to the patient. In general, the diagnostic window for evaluating differential pressure across a stenosis without the use of a hyperemic agent is identified based on characteristics and/or components of one or more of proximal pressure measurements, distal pressure measurements, proximal velocity measurements, distal velocity measurements, ECG waveforms, and/or other identifiable and/or measurable aspects of vessel performance. In that regard, various signal processing and/or computational techniques can be applied to the characteristics and/or components of one or more of proximal pressure measurements, distal pressure measurements, proximal velocity measurements, distal velocity measurements, ECG waveforms, and/or other identifiable and/or measurable aspects of vessel performance to identify a suitable diagnostic window.

In some embodiments, the determination of the diagnostic window and/or the calculation of the pressure differential are performed in approximately real time or live to identify the section 212 and calculate the pressure differential. In that regard, calculating the pressure differential in "real time" or "live" within the context of the present disclosure is understood to encompass calculations that occur within 10 seconds of data acquisition. It is recognized, however, that often "real time" or "live" calculations are performed within 1 second of data acquisition. In some instances, the "real time" or "live" calculations are performed concurrent with data acquisition. In some instances the calculations are performed by a processor in the delays between data acquisitions. For example, if data is acquired from the pressure sensing devices for 1 ms every 5 ms, then in the 4 ms between data acquisitions the processor can perform the calculations. It is understood that these timings are for example only and that data acquisition rates, processing times, and/or other parameters surrounding the calculations will vary. In other embodiments, the pressure differential calculation is performed 10 or more seconds after data acquisition. For example, in some embodiments, the data utilized to identify the diagnostic window and/or calculate the pressure differential are stored for later analysis.

By comparing the calculated pressure differential to a threshold or predetermined value, a physician or other treating medical personnel can determine what, if any, treatment should be administered. In that regard, in some instances, a calculated pressure differential above a threshold value (e.g., 0.80 on a scale of 0.00 to 1.00) is indicative of a first treatment mode (e.g., no treatment, drug therapy, etc.), while a calculated pressure differential below the threshold value is indicative of a second, more invasive treatment mode (e.g., angioplasty, stent, etc.). In some instances, the threshold value is a fixed, preset value. In other instances, the threshold value is selected for a particular patient and/or a particular stenosis of a patient. In that regard, the threshold value for a particular patient may be based on one or more of empirical data, patient characteristics, patient history, physician preference, available treatment options, and/or other parameters.

In that regard, the coloring and/or other visually distinguishing aspect of the physiology values (e.g., pressure differential measurements) can be based on the threshold value. An index or severity key showing the colors and their corresponding physiological values can be provided to the user. For example, a first color (e.g., green, medium grey, or otherwise) is utilized to represent values well above the threshold value (e.g., where the threshold value is 0.80 on a scale of 0.00 to 1.00, values above 0.85), a second color (e.g., yellow, white, or otherwise) is utilized to represent values near but above the threshold value (e.g., where the threshold value is 0.80 on a scale of 0.00 to 1.00, values between 0.82 and 0.84), a third color (e.g., orange, light grey, or otherwise) is utilized to represent values near the threshold value (e.g., where the threshold value is 0.80 on a scale of 0.00 to 1.00, values between 0.79 and 0.81), and a fourth color (e.g., red, dark grey, or otherwise) is utilized to represent values equal to or below the threshold value (e.g., where the threshold value is 0.80 on a scale of 0.00 to 1.00, values of 0.79 and below). It is appreciated that any number of color combinations, scalings, categories, and/or other characteristics can be utilized to visually represent the relative value of the pressure differential to the threshold value. However, for the sake of brevity, the numerous variations will not be individually described.

In some embodiments, the heat map included in FIG. 10, for example, is based on a cumulative or total pressure differential, where the color selected for a particular point is determined based on the pressure differential between the instrument at that point being moved through the vessel and the stationary or fixed instrument. In other embodiments, the heat map is based on localized pressure differential, where the color selected for a particular point is determined based on differences between the pressure differential of that point with one or more of the surrounding points. In that regard, the localized pressure differential is calculated as the difference between the immediately preceding point in some instances. For example, the localized pressure differential for point $P_n$ is equal to the cumulative or total pressure differential for point $P_n$ minus the total or cumulative pressure differential for point $P_{n-1}$. In other instances, the localized pressure differential is calculated as the difference between that point and a point a fixed amount of time (e.g., 10 ms, 5 ms, 2 ms, 1 ms, or otherwise) or distance (e.g., 10 mm, 5 mm, 2 mm, 1 mm, or otherwise) away from that point. By utilizing a localized pressure differential the location of significant changes in pressure differential values, which are often associated with the presence of a lesion or stenosis, can be identified.

The enhanced angiographic images can also identify transition points or areas of the vessel wherein the physiology values between portions of the vessel change by a threshold amount. In some embodiments, the threshold amount can be fixed, while in other embodiments, the threshold amount can vary between patients. The one or more transition points can be indicated by visualizations on the angiographic image. For example, markings such as tick marks extending transversely across the vessel can be utilized to signify a transition point. In other embodiments, the markings can take different shapes (e.g., circles, squares, etc.), be in different positions relative to the vessel (beside, within, etc.), be differently sized, etc. The transition points can be representative of a boundary of a lesion or stenosis of the vessel that results in an increased or decreased pressure differential, which is illustrated by the change in color of the vessel. As a result, the visualizations of the intravascular measurements (e.g., the numerical representation of the intravascular measurements, changes in color, markings, etc.) can be utilized to both identify the location of the lesion or stenosis within the vessel and assess the severity of the lesion or stenosis.

Figure 11:
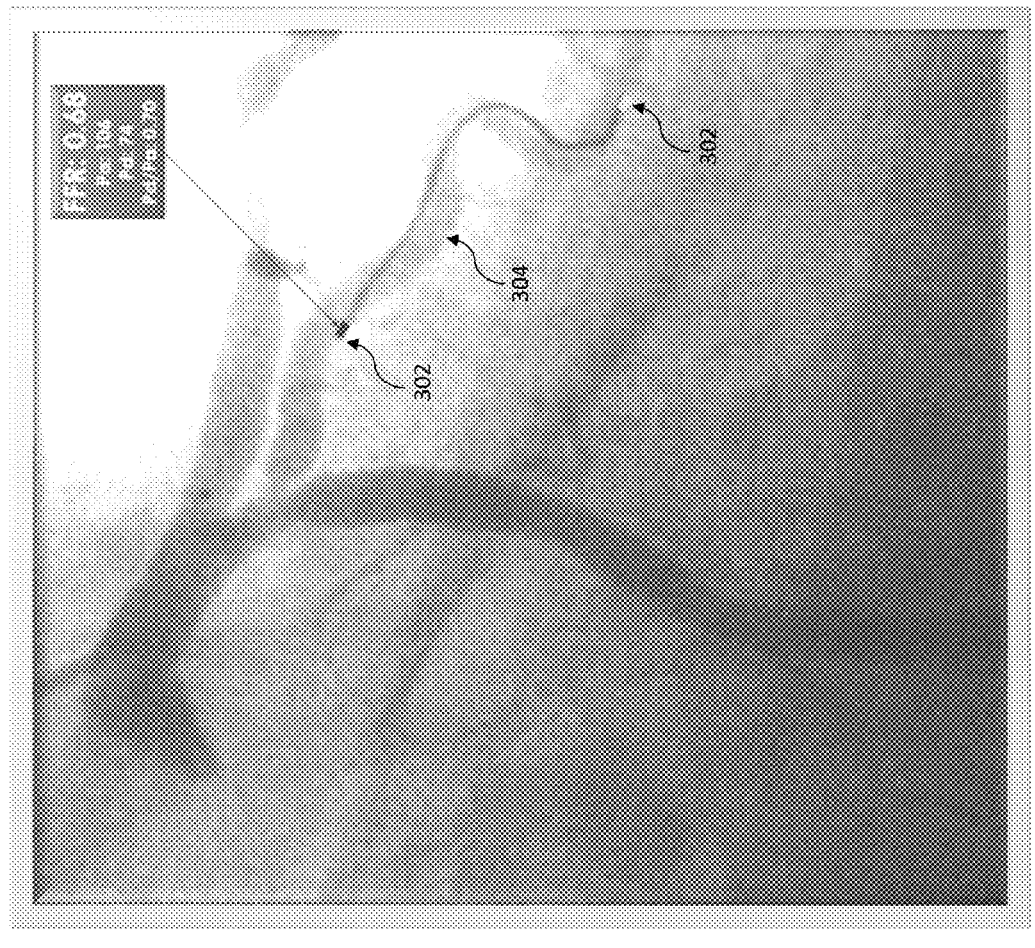
FIG. 11 is an enhanced angiographic image of a vessel according to an embodiment of the present disclosure.
Figure 12:
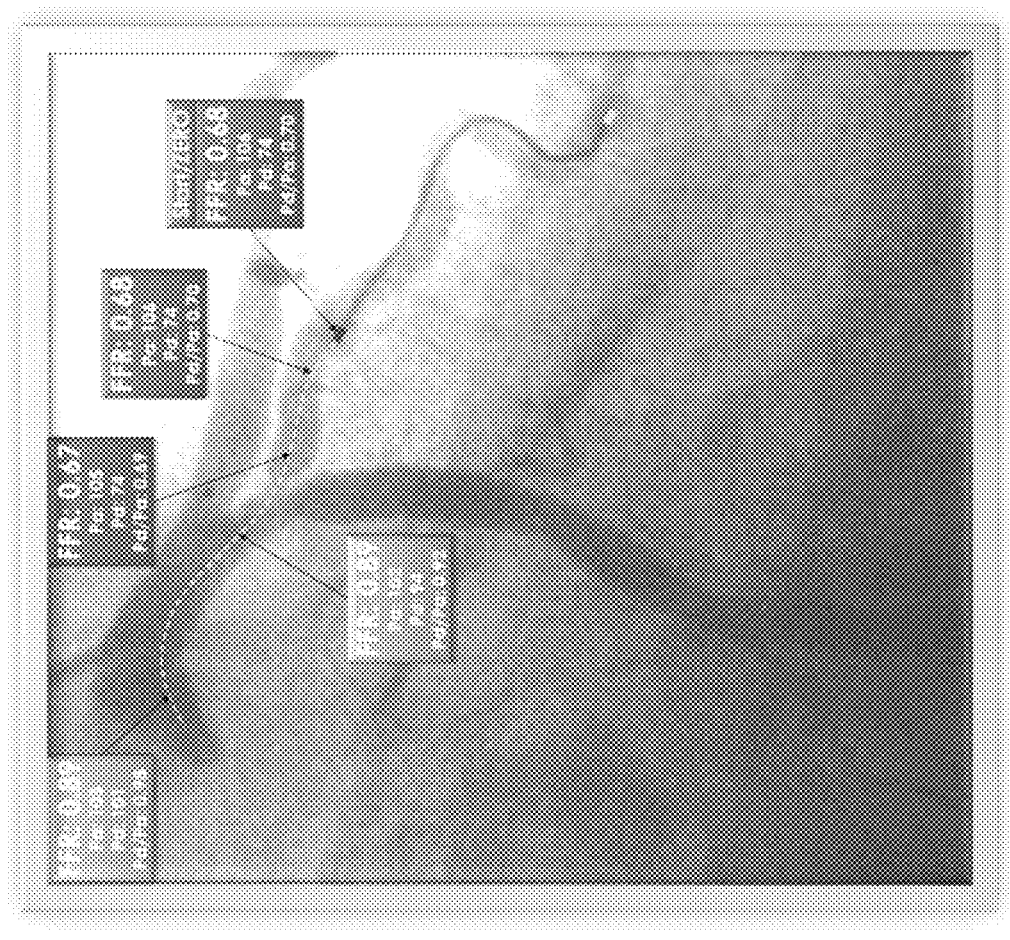
FIG. 12 is an enhanced angiographic image of a vessel according to an embodiment of the present disclosure.

Value indicators or numerical representations of the intravascular instruments can also be displayed on the intravascular image to indicate the location within the patient's vasculature to which the measurement corresponds. In that regard, the value indicators can be displayed proximate to the corresponding portion of the vessel or displayed further away from the corresponding portion of the vessel but with an additional visual element (e.g., an arrow, a straight line, a curved line, etc.) to indicate the location of the measurement. For example, FIG. 11 shows an enhanced angiographic image 360 with an FFR calculation and associated proximal and distal pressure measurements and ratio displayed with an arrow identifying the corresponding location on the angiographic image. Similarly, FIG. 12 shows an enhanced angiographic image 370 with FFR calculations and associated proximal and distal pressure measurements and ratios displayed with an arrow identifying the corresponding location at multiple locations along the length of the vessel associated with the pullback of the intravascular instrument. The color of the text or surrounding box of the intravascular data can be color coded in a similar manner to the heat map such that the color of the intravascular data in addition to the actual value can provided an indication to the user as to the severity of the lesion.

In some embodiments, the value indicators include only the value of the physiological measurement (e.g., "0.96"), while in other embodiments, the value indicators 204 include the value and type of physiological measurement (e.g., "0.95 FFR"). In yet other embodiments, additional information, such as the time the measurement was taken, severity of the stenosis or lesion, etc. can also be provided. For example, a user may provide a user input (e.g., a selection from a drop-down menu, toggle through the available options, etc.) selecting the types of information that should be displayed in value indicators. Labels, for each of the value indicators, can also be provided. Labels can include alphabetical, numeric, and/or other symbolic characters. Labels may assist in identifying markings and/or value indicators (e.g., to distinguish between different markings/value indicators and/or to facilitate discussion of the vessel depictions). The labels can be textual indications providing the names of major and/or minor vessels or segments thereof. The labels can include alphabetical, numeric, and/or other symbolic characters. In some embodiments, labels can correspond to a listing of parts of patient's vasculature.

In some embodiments, markings and/or value indicators can be positioned automatically. The system can be configured to select locations within the vessel that are clinically significant based on the intravascular information obtained (e.g., locations where the physiology value changes significantly). In some embodiments, markings can be moved along the length of the vessel. For example, a user may provide a user input (e.g., click and drag the marking, click the marking to select it and then click a new location to which it should move, etc.) to cause movement of the markings. Value indicators may be correspondingly updated with data that is based on the new location and/or move based on new location. That is, value indicators can display diagnostic information along the length of the vessel. In this manner, a user may select a region of interest of the vessel by moving marking and/or value indicator to indicate an area of a vessel with a higher pressure differential, a lesion, and/or stenosis.

In some embodiments, visualizations to indicate a region of interest include multiple markings and a connector between the markings. In some embodiments, the markings may be individually moved and the connector corresponding lengthens or shortens to span the space between them. In other embodiments, the markings and connector are collectively translated along the vessel with a fixed length or spacing between them.

Figure 13:
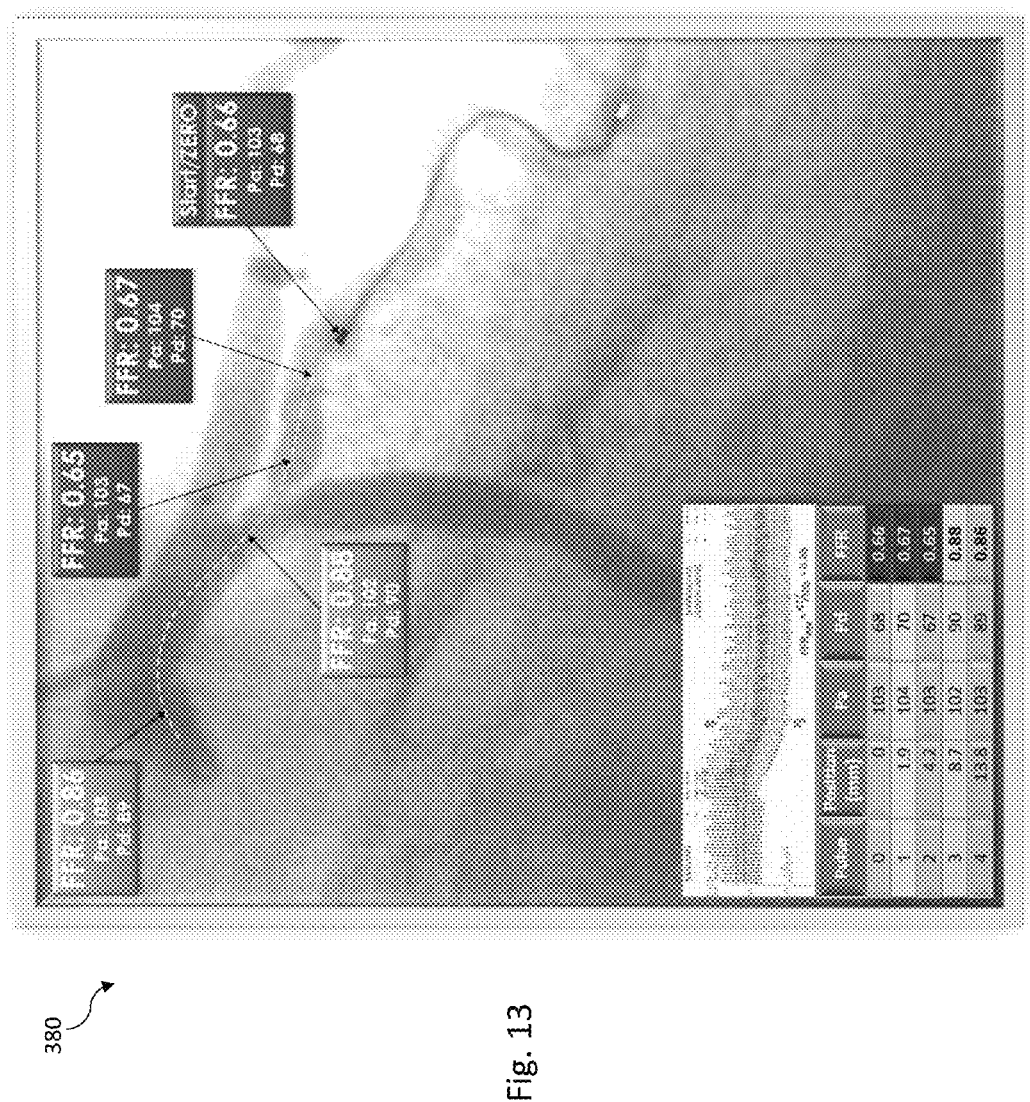
FIG. 13 is an enhanced angiographic image of a vessel according to an embodiment of the present disclosure.

Referring now to FIG. 13, shown therein is an enhanced angiographic image 380 that includes FFR calculations and associated proximal and distal pressure measurements and ratios along with a corresponding pressure graph of the underlying proximal and distal pressure measurements and the chart of intravascular information used to make the calculations and/or co-register the intravascular information to the angiographic image. The pressure graph and chart are exemplary in nature and simply represent the fact that in some embodiments the intravascular information is presented in a more traditional format over a portion of the angiographic image. As discussed below, in some instances, a user is able to select what intravascular information and in what format will be displayed on the enhanced angiographic image.

One or more images of a vessel, the visualizations in those images, and/or the measured physiological values can be used to evaluate whether and/or how to perform a surgical procedure. For example, the measured physiological values and/or the images of the vessels, which indicate the location, extent, and severity of one or more lesions or stenoses, can be used to predict probabilities of different treatment options. The regions of interest can be used to determine how and/or where in the vasculature to intervene. For example, the location, extent, and severity of one or more lesions or stenoses, can be used to estimate the number of stents, the length of stents, etc. The physiological values can also be used to calculate a numerical or otherwise objective indication of risk/benefit, as described herein. The objective indication of risk/benefit can be used to evaluate whether and/or how to perform a surgical procedure.

The one or more visualizations of can include or be supplemented with information regarding characteristics of the lesion or stenosis and/or the vessel using one or more other vessel data-gathering modalities. The other representations of the lesion or stenosis and/or the vessel can include, e.g., IVUS (including virtual histology), OCT, ICE, Thermal, Infrared, flow, Doppler flow, and/or other vessel data-gathering modalities. The additional information can provide a more complete and/or accurate understanding of the vessel characteristics and/or assist in evaluating a risk associated with a lesion or stenosis. For example, in some instances the information can include the occlusive value of the vessel. The occlusive value of the vessel and/or other additional information may be utilized to calculate an objective measure of the risk associated with the stenosis or lesion.

Figure 14:
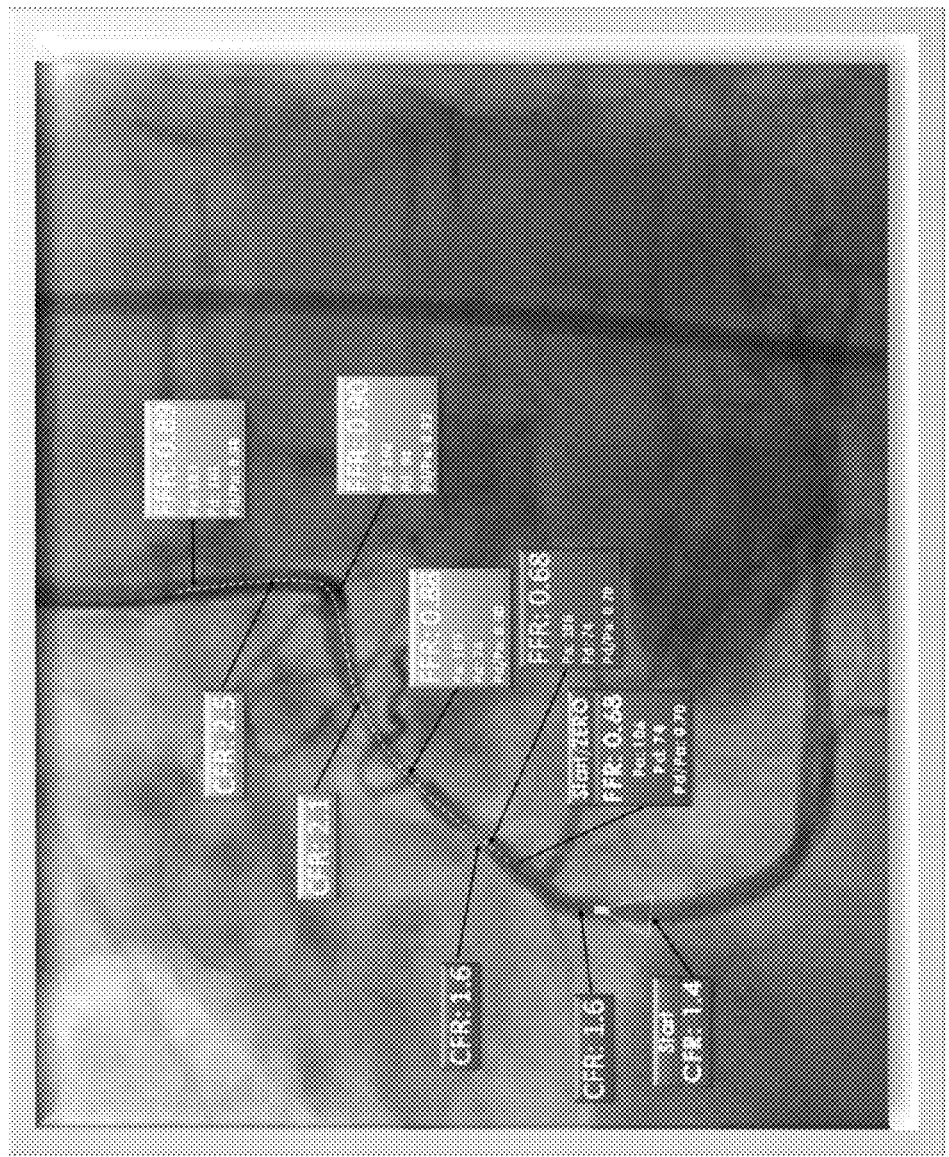
FIG. 14 is an enhanced angiographic image of a vessel according to an embodiment of the present disclosure.
Figure 15:
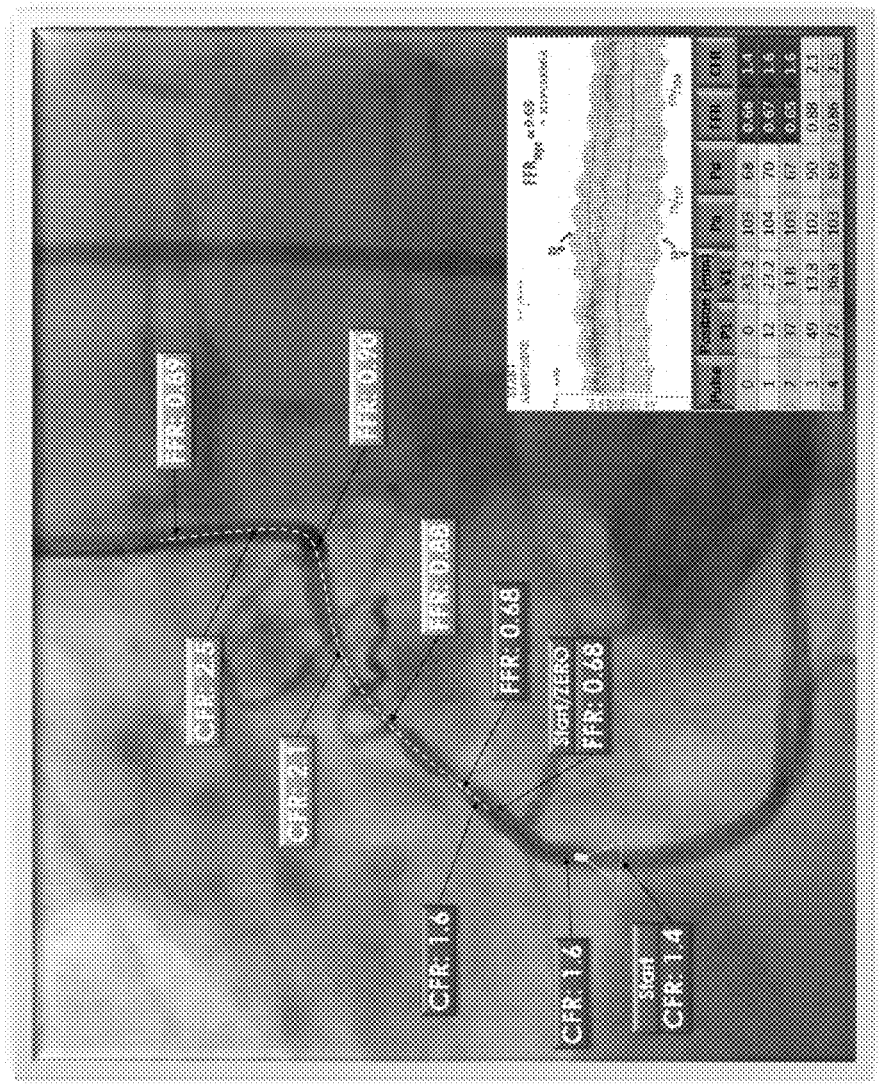
FIG. 15 is an enhanced angiographic image of a vessel according to an embodiment of the present disclosure.

Referring to FIGS. 14 and 15, shown therein are enhanced angiographic images that include visualizations based on both pressure measurements and flow measurements. In particular, FIG. 14 shows an enhanced angiographic image 390 having both CFR and FFR calculations displayed with an arrow identifying the corresponding location at multiple locations along the length of the vessel associated with the pullback of the intravascular instrument. FIG. 15 shows an enhanced angiographic image 400 with similar features, but also including a graph of corresponding pressure measurements, flow measurements, and/or a chart of the intravascular information used to make the calculations and/or co-register the intravascular information to the angiographic image.

It is understood that numerous other visualization techniques may be utilized to convey the information in the context of an angiographic image or other image of the vessel (including both intravascular and extravascular imaging techniques, such as IVUS, OCT, ICE, CTA, etc.) to help the user evaluate the vessel. In that regard, while the examples of the present disclosure are provided with respect to angiographic images, it is understood that the concepts are equally applicable to other types of vessel imaging techniques, including intravascular and extravascular imaging In some instances, a user is able to select what information should be included or excluded from the displayed image. In that regard, it should be noted that these visualization techniques related to conveying the pressure measurement data in the context of an angiographic or other image of the vessel can be utilized individually and in any combinations. For example, in some implementations a user is able to select what visualization mode(s) and/or portions thereof will be utilized and the system outputs the display accordingly. Further, in some implementations the user is able to manually annotate the displayed image to include notes and/or input one or more of the measured parameters. In some instances, the user has the option to either show or hide the graphs, tables, and/or other data corresponding to the overlaid physiological data. To this end, the user may click or otherwise select to display the graphs, tables, and/or other data, including zooming in on particular relevant data or other information of interest to the user.

The images of vessels can include three-dimensional, two-dimensional, angiographic, a computed tomography angiographic (CTA), and/or other suitable forms of images. In some embodiments, a three-dimensional image may be rotated about a vertical axis. In some embodiments, a two-dimensional image may include multiple views about a vertical axis such that different two-dimensional views are shown when the image is rotated. In some implementations, the three dimensional model is displayed adjacent to a corresponding two dimensional depiction of the vessel. In that regard, the user may select both the type of depiction(s) (two dimensional (including imaging modality type) and/or three dimensional) along with what visualization mode(s) and/or portions thereof will be utilized. The system will output a corresponding display based on the user's preferences/selections and/or system defaults.

Those skilled in the art will recognize that the features described above can be implemented in a many different ways, dependent upon various factors such as user preference, targeted physiology, type(s) of intravascular instrument(s) utilized, available processing resources, procedure time, etc. However, an exemplary technique for creating an enhanced angiographic image with overlaid physiological measurements according to embodiments of the present disclosure will now be described. The result is a compound image (or a series of images) constructed to highlight the radiopaque locations and/or the attendant physiology measurements using selected symbol settings. It is understood that the steps described below may be performed in a different order, include additional steps, omit steps described, and/or otherwise be modified without departing from the scope of the present disclosure.

In some instances, the method begins by allowing a user to define the physiology overlay display settings. That is, a user defines what information and in what format should be displayed. The system may include default settings, group settings, and/or individual settings. The group settings allow a group of users to share display settings. Multiple groups can be defined, each with custom settings. Similarly, the individual settings allow an individual user to have custom display settings. Again, multiple individuals can be defined, each with custom settings. The overlay settings can be utilized to set the display parameters for any of the features described in the present application. For sake of brevity, a few options will be described. For example, an individual or group can select how to enhance the vascular location and display the physiology measurement(s) on the angiographic image using unique symbols (arrow, circle, Pd, FFR, CFR, FFR/CFR, etc.), symbol combinations (arrow/FFR, arrow/CFR, etc.), symbol colors, symbol actions (on, fade-in/fade-out, strobe, etc.), etc.

With the initial physiology overlay display settings defined, an intravascular instrument is positioned within the anatomy and utilized to obtain intravascular information. In some instances, an optional hyperemic drug is administered. With the physiological overlay activated (via button, voice command, etc.), the system calculates the pixel location and uniquely identifies every radiopaque element of the intravascular instrument relative to the angiographic image(s) within the display. In some implementations, multiple radiopaque elements on the same guide wire can be uniquely identified (length, radiopacity, etc.). The intravascular information or physiology is measured with the intravascular instrument and the intravascular/physiology measurement is associated with the two-dimensional display location that corresponds to the radiopaque element that is the sensor location (or sensor focal point). Generally, duplicate images (i.e., where the location of radiopaque elements is the same or "equal") may generally be ignored. The pre-selected symbol(s) from the selected physiology overlay display settings is then superimposed on the angiographic image at the two-dimensional display location identified. Optionally, the compound image and associative elements (time-stamp, angiographic orientation, etc.) may be saved as a new single element separate from the separate underlying data. This procedure is repeated for each heartbeat (or other common interval) as the intravascular instrument is moved through the vessel. In some instances, data is captured once per heartbeat. The compound image(s) are then displayed to the user. In some instances, multiple compound images are provided using different underlying angiographic images obtained during movement of the intravascular device. In some instances, the different angiographic images are from different orientations to allow alternative views of the vessel. For example, bi-plane angiography is utilized in some instances.

Aspects of the present disclosure provide: (1) a comprehensive map of focal and/or diffuse stenosis severity for a targeted vascular region; (2) a demonstration that CFR is linearly related to FFR for progressive stenosis superimposed on diffuse narrowing; (3) a demonstration that the relative contributions of focal and diffuse disease define the slope and values along the linear CFR and FFR relationship; and (4) a showing that discordant CFR and FFR values reflect divergent extremes of focal and diffuse disease, not failure of either tool.

Persons skilled in the art will also recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A method of evaluating a vessel of a patient, comprising:
    obtaining distal intravascular pressure data from a first intravascular pressure-sensing instrument positioned within a vessel of a patient while the first intravascular pressure-sensing instrument is moved longitudinally through the vessel from a first position to a second position, the first intravascular pressure-sensing instrument including a radiopaque element;
    obtaining proximal intravascular pressure data from a second intravascular pressure-sensing instrument positioned within the patient while the first intravascular pressure-sensing instrument is moved longitudinally through the vessel and the second intravascular pressure-sensing instrument is maintained in a fixed location within the vessel;
    obtaining an angiographic image of the vessel while the first intravascular pressure-sensing instrument is moved longitudinally through the vessel, wherein the angiographic image comprises the radiopaque element at corresponding locations within the vessel while the first intravascular pressure-sensing instrument is moved longitudinally through the vessel;
    correlating, for each heartbeat cycle of the patient, the distal intravascular pressure data from the first intravascular pressure-sensing instrument to a particular location of the vessel on the angiographic image based on the location of the radiopaque element within the vessel in the angiographic image;
    calculating, for each heartbeat cycle of the patient, a pressure ratio of the obtained distal intravascular pressure data to the obtained proximal intravascular pressure data at the correlated location for each heartbeat cycle, wherein the pressure ratio is calculated using the distal intravascular pressure data and the proximal intravascular pressure data obtained during a diagnostic window that encompasses only a portion of each heartbeat cycle of the patient;
    storing, in a memory, the calculated pressure ratio for each heartbeat cycle with the correlated location for the heartbeat cycle; and
    outputting an enhanced angiographic image of the vessel on a display, the enhanced angiographic image including the angiographic image overlaid with visualizations representing:
        an indicator showing the correlated location along the vessel; and
        the pressure ratio of the obtained distal intravascular pressure data to the obtained proximal intravascular pressure data at the correlated location for each heartbeat cycle,
    wherein the visualizations include a numerical value of the pressure ratio adjacent to the indicator of the correlated location for each heartbeat cycle on the angiographic image.

2. The method of claim 1, wherein the first position is distal of at least one stenosis of the vessel.

3. The method of claim 2, wherein the second position is proximal of the at least one stenosis of the vessel such that moving the second instrument longitudinally through the vessel comprises a pullback.

4. The method of claim 1, further comprising obtaining intravascular flow data from the intravascular pressure-sensing instruments positioned within the vessel of the patient.

5. The method of claim 4, wherein the enhanced angiographic image further includes visualizations representing a calculated flow ratio.

6. The method of claim 1, wherein the angiographic image is at least one of a two dimensional angiographic image, a three dimensional angiographic image, and a computed tomography angiographic (CTA) image.

7. The method of claim 1, wherein the visualizations further include an intensity map based on changes in the ratio of the distal intravascular pressure data to the proximal intravascular pressure data as the first intravascular pressure-sensing instrument is moved longitudinally through the vessel.

8. The method of claim 7, wherein a first visual characteristic of the intensity map is associated with the ratio of the distal intravascular pressure data to the proximal intravascular pressure data being above a threshold value and a second visual characteristic of the intensity map is associated with the ratio of the distal intravascular pressure data to the proximal intravascular pressure data being below the threshold value.

9. The method of claim 8, wherein the first visual characteristic is a first color and the second visual characteristic is a second color visually distinguishable from the first color.

10. A system for evaluating a vessel of a patient, comprising:
    a first intravascular pressure-sensing instrument sized and shaped for introduction into the vessel of the patient, the first intravascular pressure-sensing instrument including a radiopaque element;
    a processing system in communication with the first intravascular pressure-sensing instrument, a second intravascular pressure-sensing instrument, an external imaging system, and a display, the processing system configured to:
        obtain distal intravascular pressure data obtained by the first intravascular pressure-sensing instrument while positioned within a vessel of a patient and moved longitudinally through the vessel from a first position to a second position;

obtain proximal intravascular pressure data obtained by the second intravascular pressure-sensing instrument while positioned at a fixed location within the patient while the first intravascular pressure-sensing instrument is moved longitudinally through the vessel;

obtain an angiographic image of the vessel obtained by the external imaging system while the first intravascular pressure-sensing instrument was moved longitudinally through the vessel, wherein the angiographic image comprises the radiopaque element at corresponding locations within the vessel while the first intravascular pressure-sensing instrument is moved longitudinally through the vessel;

correlate, for each heartbeat cycle of the patient, the distal intravascular pressure data from the first intravascular pressure-sensing instrument to a particular location of the vessel on the angiographic image based on a location of the radiopaque element within the vessel in the angiographic image;

calculate, for each heartbeat cycle of the patient, a pressure ratio of the obtained distal intravascular pressure data to the obtained proximal intravascular pressure data at the correlated location for each heartbeat cycle, wherein the pressure ratio is calculated using the distal intravascular pressure data and the proximal intravascular pressure data obtained during a diagnostic window that encompasses only a portion of each heartbeat cycle of the patient;

store, in a memory, the calculated pressure ratio for each heartbeat cycle with the correlated location for the heartbeat cycle; and output an enhanced angiographic image of the vessel on the display, the enhanced angiographic image including the angiographic image overlaid with visualizations representing:
   an indicator showing the correlated location along the vessel; and
   the pressure ratio of the obtained distal intravascular pressure data to the obtained proximal intravascular pressure data at the correlated location for each heartbeat cycle,
   wherein the visualizations include a numerical value of the pressure ratio adjacent to the indicator of the correlated location for each heartbeat cycle, on the angiographic image.

11. The system of claim 10, wherein the processing system is further configured to obtain intravascular flow data from the intravascular pressure-sensing instruments positioned within the vessel of the patient.

12. The system of claim 11, wherein the processing system is further configured to output the enhanced angiographic image with visualizations representing a calculated flow ratio.

13. The system of claim 10, wherein the first intravascular pressure-sensing instrument is a guidewire.

14. The system of claim 13, wherein the second intravascular pressure-sensing instrument is a catheter.

15. The system of claim 10, wherein the visualizations further include an intensity map based on changes in the ratio of the distal intravascular pressure data to the proximal intravascular pressure data as the first intravascular pressure instrument is moved longitudinally through the vessel.

16. The system of claim 15, wherein a first visual characteristic of the intensity map is associated with the ratio of the distal intravascular pressure data to the proximal intravascular pressure data being above a threshold value and a second visual characteristic of the intensity map is associated with the ratio of the distal intravascular pressure data to the proximal intravascular pressure data being below the threshold value.

17. The system of claim 16, wherein the first visual characteristic is a first color and the second visual characteristic is a second color visually distinguishable from the first color.

18. The system of claim 10, wherein the visualizations further include a second pressure ratio of the obtained distal intravascular pressure data to the obtained proximal intravascular pressure data at the correlated location for each heartbeat cycle, wherein the visualizations include a numerical value of the second pressure ratio.

19. A system for evaluating a vessel of a patient, comprising:
   a first intravascular instrument configured to obtain pressure and flow data, wherein the first intravascular instrument is sized and shaped for introduction into the vessel of the patient, the first intravascular instrument including a radiopaque element;
   a processing system in communication with the first intravascular instrument, a second intravascular instrument, an external imaging system, and a display, the processing system configured to:
      obtain distal pressure data obtained by the first intravascular instrument while positioned within a vessel of a patient and moved longitudinally through the vessel from a first position to a second position;
      obtain proximal pressure data obtained by the second intravascular instrument while positioned at a fixed location within the patient while the first intravascular instrument is moved longitudinally through the vessel;
      obtain flow data obtained by the first intravascular instrument while positioned within the vessel of the patient;
      obtain an angiographic image of the vessel obtained by the external imaging system while the first intravascular instrument was moved longitudinally through the vessel, wherein the angiographic image comprises the radiopaque element at corresponding locations within the vessel while the first intravascular instrument is moved longitudinally through the vessel;
      correlate, for each heartbeat cycle of the patient, the distal pressure data and the flow data from the first intravascular instrument to a respective location of the vessel on the angiographic image based on a location of the radiopaque element within the vessel in the angiographic image; and
      output an enhanced angiographic image of the vessel on the display, the enhanced angiographic image including the angiographic image overlaid with visualizations representing:
         an indicator showing the correlated location along the vessel;
         a pressure ratio of the obtained distal intravascular pressure data to the obtained proximal intravascular pressure data at the correlated location for each heartbeat cycle; and
         a flow ratio based on the obtained flow data, wherein the flow ratio comprises a measure of a volume of blood flow within the vessel, wherein the visualizations include a numerical value of the pressure ratio and a numerical value of flow ratio, wherein the numerical values are adjacent to the indicator of the correlated location for each heartbeat cycle on the angiographic image.

20. The system of claim 19, wherein the numerical value of the pressure ratio is positioned adjacent to the vessel at different locations along the vessel than the numerical value of the flow ratio.

* * * * *